(12) United States Patent
Rapraeger et al.

(10) Patent No.: US 9,963,498 B2
(45) Date of Patent: May 8, 2018

(54) PEPTIDES THAT INHIBIT SYNDECAN-1 ACTIVATION OF VLA-4 AND IGF-1R

(71) Applicant: Wisconsin Alumni Research Foundation, Madison, WI (US)

(72) Inventors: Alan C. Rapraeger, Stoughton, WI (US); DeannaLee M. Beauvais, Monona, WI (US); Oisun Jung, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days. days.

(21) Appl. No.: 15/680,423

(22) Filed: Aug. 18, 2017

(65) Prior Publication Data
US 2018/0086813 A1  Mar. 29, 2018

Related U.S. Application Data

(60) Provisional application No. 62/376,528, filed on Aug. 18, 2016.

(51) Int. Cl.
| | | |
|---|---|---|
| *A61K 38/00* | (2006.01) | |
| *C07K 14/705* | (2006.01) | |
| *A61K 45/06* | (2006.01) | |
| *A61K 38/17* | (2006.01) | |

(52) U.S. Cl.
CPC ...... *C07K 14/70596* (2013.01); *A61K 38/177* (2013.01); *A61K 45/06* (2013.01); *C07K 2319/74* (2013.01)

(58) Field of Classification Search
None
See application file for complete search history.

(56) References Cited

U.S. PATENT DOCUMENTS

2008/0020979 A1* 1/2008 Rapraeger ............ C07K 14/705
514/1.9
2014/0011764 A1   1/2014 McGuigan et al.

OTHER PUBLICATIONS

Haiyao Wang et al., "Syndecan-1 and Syndecan-4 Capture Epidermal Growth Factor Receptor Family Members and the [alpha]3[beta]1 Integrin Via Binding Sites in Their Ectodomains: Novel Synstatins Prevent Kinase Capture and Inhibit [alpha]6[beta]4-Integrin-Dependent Epithelial Cell Motility," Journal of Biological Chemistry, vol. 290. No. 43, Oct. 23, 2015, pp. 26103-26113.
O Jung et al., "Heparanase-induced shedding of syndecan-1/CD138 in myeloma and endothelial cells activates VEGFR2 and an invasive phenotype: prevention by novel synstatins," Oncogenesis, vol. 5, No. 2, Feb. 29, 2016, pp. 1-13.
Alan C. Rapraeger et al., "Vasular endothelial-cadherin stimulates syndecan-1-coupled insulin-like growth factor-1 receptor and crosstalk between [alpha]V[beta]3 integrin and vascular endothelial growth factor receptor 2 at the onset of endothelial cell dissemination during angiogenesis," Febs Journal, vol. 280, No. 10, Feb. 11, 2013, pp. 2194-2206.

* cited by examiner

*Primary Examiner* — Jeanette M Lieb
(74) *Attorney, Agent, or Firm* — Boyle Fredrickson S.C.

(57) ABSTRACT

A fusion peptides with sequences derived from the extracellular domain of syndecan-1 that inhibits VLA-4 and IGF-1R signaling are disclosed. The fusion peptides include an IGF-1R-binding segment having the amino acid sequence LPAGEGPKEGEAVVLPEVEPGLTAREQ (SEQ ID NO:1) and a VLA-4-binding segment having the amino acid sequence sequence DFTFETSGENTA (SEQ ID NO:2).

20 Claims, 28 Drawing Sheets

| Sequence | Activity (%) |
|---|---|
| ⁸⁹STST-LPAGEGPKEGEAVVLPEVEPGLTAREQE¹²⁰ | 100 |
| LPAGEGPKEGEAVVLPEVEPGLTAREQ | 20 |
| LPAGEGPKEGEAVVLPEVEPGLTARE | 10* |
| LPAGEGPKEGEAVVLPEVEPGLTAR | <1* |
| PAGEGPKEGEAVVLPEVEPGLTAREQE | 20 |
| AGEGPKEGEAVVLPEVEPGLTAREQE | <1* |
| Human SSTN$_{IGF1R}$   LPAGEGPKEGEAVVLPEVEPGLTAREQE | 100 |

SHORTEST SEQUENCE WITH FULL ACTIVITY

Fig. 3

| Sequence | Activity (%) |
|---|---|
| $^{210}$DFTFETSGENTAVVAVEPDRRNQSPVDQGAT$^{240}$ | 100* |
| ETSGENTAVVAVEPDRRNQSPVDQGAT | <1 |
| DFTFETSGENTAVVAVEPDRRNQSPVD | 100* |
| DFTFETSGENTAVVAVEPDRRNQS | 100 |
| ETSGENTAVVAVEPDRRNQS | <1 |
| DFTFETSGENTA | 100 |
| Human SSTN$_{VLA4}$ $^{210}$DFTFETSGENTA$^{221}$ | 100 |

SHORTEST SEQUENCE WITH FULL ACTIVITY

Fig. 12

|  | C-terminus of SSTN$_{IGF1R}$ | 4 upstream amino acids and N-terminus of SSTN$_{VLA4}$ |
|---|---|---|
| HUMAN | ....$^{113}$GLTAREQE$^{120}$ | $^{206}$SGEQDFTF.... |
| MOUSE | ....$^{112}$GFTARDKE$^{119}$ | $^{207}$SGEQDFTF.... |
| RAT | ....$^{113}$DFTARDKE$^{120}$ | $^{205}$SGEQDFTF.... |
| MACAQUE | ....$^{113}$DLTAREQE$^{120}$ | $^{206}$SGEQDFTF.... |
| GIBBON | ....$^{113}$GLTAREEE$^{120}$ | $^{213}$SGEQDFTF.... |
| HAMSTER | ....$^{113}$SSTTWDKE$^{120}$ | $^{205}$SGEQDFTF.... |
| ORCA | ....$^{113}$GLTAQEKE$^{120}$ | $^{207}$SGEQDFTF.... |

SSTN-IGF1R    $^{93}$LPAGEGPKEGEAVVLPEVEPGLTAREQE$^{120}$
SSTN-VLA4                              $^{208}$EQDFTFETSGENTA$^{221}$
new SSTN-I/V  $^{93}$LPAGEGPKEGEAVVLPEVEPGLTAREQDFTFETSGENTA$^{221}$

- Retains activity of SSTN-IGF1R
  very stable
  kills myeloma cells
- Retains activity of SSTN-VLA4
  very stable
  blocks VLA-4-mediated adhesion of myeloma cells
  blocks VLA-4-mediated adhesion of endothelial cells

Fig. 13C

| | Inhibit VLA4: |
|---|---|
| LPAGEGPKEGEAVVLPEVEPGLTAREQEAAAADFTFETSGENTAVVAVEPDRRRNQS | + |
| LPAGEGPKEGEAVVLPEVEPGLTAREQEAAAADFTFETSGENTA | + |
| LPAGEGPKEGEAVVLPEVEPGLTAREQEAAAADFTF | − |
| LPAGEGPKEGEAVVLPEVEPGLTAREQDFTFETSGENTAVVAVEPDRRRNQS | + |
| LPAGEGPKEGEAVVLPEVEPGLTAREQDFTFETSGENTA | + |

Fig. 13D

PEPTIDES THAT INHIBIT SYNDECAN-1 ACTIVATION OF VLA-4 AND IGF-1R

CROSS REFERENCE TO RELATED APPLICATIONS

This application claims the benefit of U.S. provisional Application No. 62/376,528 filed on Aug. 18, 2016, which is incorporated by reference herein in its entirety.

STATEMENT REGARDING FEDERALLY FUNDED RESEARCH

This invention was made with government support under CA139872 awarded by the National Institutes of Health. The government has certain rights in the invention.

BACKGROUND

I. Field

The present disclosure relates generally to the fields of oncology, medicine and cell biology. More particularly, it concerns peptide segments from the extracellular domain of syndecan-1 (Sdc-1) that can inhibit binding to and activation of VLA-4 and IGF-1R, and can thus block cell survival and invasion of numerous cancer cells, tumor-induced angiogenesis, and homing of leukocytes in immune diseases, solid tumors and lymphomas/leukemias/myeloma.

II. Description of Related Art

Cell surface adhesion receptors physically bind cells to their extracellular matrix (ECM) and couple such interactions to intracellular signaling mechanisms that influence gene expression, cell morphology, motility, growth, differentiation and survival (Roskelley et al., 1995; Miranti and Brugge, 2002). Many ECM ligands contain closely spaced proteoglycan- and integrin-binding domains, indicating that the molecular mechanisms by which cells recognize and interact with their extracellular milieu may involve the formation of signaling complexes containing both proteoglycans and integrins. Consequentially, these two types of receptors may act in concert to modulate cell adhesion and migration.

A. Syndecans

The vertebrate syndecans are a family of four transmembrane heparan sulfate proteoglycans (HSPGs) (Sdc1-4) (FIG. 1). One or more syndecans are expressed on all cells, with the possible exception of some lymphocytes, although their expression may be altered in disease states such as cancer (Beauvais and Rapraeger, 2004a). Endowed by their heparan sulfate (HS) chains, syndecans bind a variety of extracellular matrix (ECM) ligands, including fibronectin (FN), laminin (LN), tenascin, thrombospondin (TSP), vitronectin (VN) and the fibrillar collagens (COL) (Bemfield et al., 1999). The syndecans display a high degree of conservation within their core proteins across species and across family members.

The syndecans lack intrinsic signaling activity. Their short cytoplasmic tails (ca. 30 aa) consist of three regions, two of which are conserved amongst the four syndecans (C1 and C2) and which flank an intervening variable (V) region that is unique to each family member.

The syndecan cytoplasmic domains have roles in focal adhesion formation and in the response of syndecans to growth factor and ECM adhesion signals. Distinct roles for the V-regions of Sdc-2 and -4 in matrix assembly and focal adhesion formation respectively have been described (Klass et al., 2000; Woods and Couchman, 2001). For Sdc4, these activities trace to the unique ability of the V region to bind activated PKCα as well as phosphatidylinositol-4,5bisphosphate (PIP2), potentiating PKCα activity (Oh et al., 1997a; Oh et al., 1997b; Oh et al., 1998) which in turn affects activation of Rho and Rac GTPases. The syndecan C2 regions bind to PDZ proteins such as synectin and syntenin, which bind to signaling effectors such as Arf6 that control syndecan endocytosis, vesicle recycling, and exosome formation (Zimmermann et al. 2005, Elfenbein and Simons 2013). In addition, the inventors have shown that the cytoplasmic domain of the syndecans binds the cytoplasmic domain of the β4 integrin, part of a mechanism in which capturing the α6β4 integrin in epithelial cells and carcinomas drives cell motility (Rapraeger 2000, Wang et al. 2010, Wang et al. 2014).

The syndecan transmembrane (TM) domains are also highly conserved, and each syndecan has a set of alanines/glycines that align along one side of the domain when the TM forms a helix within the membrane, an alignment that allows protein-protein interactions within the membrane (Rapraeger 2000). Specific amino acids in the syndecan TMs promote dimerization and heterodimerization amongst the syndecans, and potentially with other membrane receptors, and appear to facilitate syndecan clustering and signaling (Rapraeger 2000, Choi et al. 2005, Choi et al. 2015, Kwon et al. 2015).

The syndecan ectodomains (EDs) are divergent with the exception of attachment sites for HS glycosaminoglycans. Via their HS chains, syndecans regulate the signaling of growth factors, chemokines, and morphogens and engage components of the ECM including VN, FN, LN, tenascin, thrombospondin, and the fibrillar COLs (Bernfield et al., 1999). More recent work from the inventors has now shown conclusively that the syndecan extracellular domains contain receptor "organizer" sites that capture other receptors, notably matrix-binding integrins and growth factor receptor tyrosine kinases. Kinases that have been shown to be captured are all critical for cancer, namely, the insulin-like growth factor-1 receptor (IGF-1R) (Beauvais and Rapraeger 2010), epidermal growth factor receptor (EGFR) (Wang et al. 2015), HER2 which is another member of the EGFR family (Wang et al. 2015), and vascular endothelial cell growth factor receptor-2 (VEGFR2) (Jung et al. 2016), which is expressed on endothelial cells and is crucial for angiogenesis, but is also aberrantly expressed on some tumors. Based on these findings, the inventors have designed peptide mimetics of the docking sites in the syndecans. These peptides, called "synstatins" or "SSTNs", compete for receptor docking with the syndecan and inhibit the ensuing signaling activities upon which tumor cells and activated endothelial cells depend, thus inhibiting tumorigenesis.

The first receptor docking site in a syndecan was shown for Sdc4 (McFall and Rapraeger, 1997; McFall and Rapraeger, 1998), identifying a region that was recognized by other cell surface receptors on fibroblasts and endothelial cells. Other groups have shown that the functionality of this site is conserved across vertebrates to zebrafish. However, recent work by the inventors shows that on epithelial cells this site causes Sdc4 to simultaneously engage EGFR and the α3β1 integrin, while the cytoplasmic domain of Sdc4 captures the α6β4 integrin (Wang et al. 2014. This quaternary receptor complex mediates the migration of epithelial cells on laminin-5, and is essential for carcinoma cell survival. A peptide based on this site (SSTN87-131 or "SSTN$_{EGFR}$") blocks this mechanism (Wang et al. 2015).

B. Co-Receptor Docking Motifs in the Extracellular Domain of Sdc1.

Although first identified in Sdc4, the most work on co-receptor docking motifs has involved Sdc1. The extracellular domain of Sdc1 contains a juxtamembrane docking site much like Sdc4, with the exception that the site in Sdc1 binds the EGFR family member HER2 and the β3β1 integrin, rather than EGFR and the integrin. This site (amino acids 210-240 in human Sdc1) can be mimicked by a peptide (SSTN210-240 or "SSTN$_{HER2}$") that displaces HER2 and α3β1 integrin from Sdc1, blocks phosphorylation of the α6β4 integrin captured by the Sdc4 cytoplasmic domain, and disrupts epithelial cell migration (Wang et al. 2010, Wang et al. 2014, Wang et al. 2015).

Three additional sites have been identified in Sdc1. One site (aa 93-120 in human Sdc1) binds the insulin-like growth factor-1 receptor (IGF-1R), together with the αvβ3 or αvβ5 integrin (Beauvais et al. 2009, Beauvais and Rapraeger 2010). This receptor complex is expressed on tumor cells and activated endothelial cells. A peptide derived from this site, called SSTN$_{IGF1R}$, blocks tumorigenesis and angiogenesis by disrupting cell invasion and cell survival (Beauvais et al, 2009; Beauvais and Rapraeger, 2010; Beauvais et al., 2016). A second site (aa210-236) binds the α4β1 integrin (known on leukocytes as "very late antigen-4" or VLA-4) and vascular endothelial cell growth factor receptor-2 (VEGFR2) (Jung et al. 2016). Within this segment, the DFTF motif (aa210-214) is essential for VLA-4 binding, and the PVD motif (aa234-236) is essential for the capture of VEGFR2. Synstatin peptides containing only one but not both of these motifs specifically compete with syndecan-1 for capture of the receptor recognized by that motif and disrupt formation of the receptor complex. Thus, peptides containing aa210-233 or 210-221 contain only the VLA-4 binding motif and these peptides, collectively called SST-N$_{VLA4}$, prevent VLA-4 from engaging with syndecan-1 and prevent activation of the integrin (Jung et al., 2016).

C. Syndecan-1

Syndecan-1 is highly expressed at the basolateral surface of epithelial cells where it is thought to modulate cell adhesion and growth factor signaling (Bernfield et al., 1999; Rapraeger et al., 1986; Kim et al., 1994; Sanderson and Bernfield, 1988). Some studies suggest that Sdc1 is a tumor suppressor. Sdc1 is reportedly downregulated in a number of epithelial cancers and in pre-malignant lesions of the oral mucosa (Soukka et al., 2000) and uterine cervix (Inki et al., 1994; Rintala et al., 1999; Nakanishi et al., 1999). Loss of Sdc-1 also correlates with reduced patient survival in squamous cell carcinoma of the head, neck and lung (Anttonen et al., 1999; Inki et al., 1994; Nakaerts et al., 1997), laryngeal cancer (Pulkkinen et al., 1997; Klatka, 2002), malignant mesothelioma (Kumar-Singh et al., 1998) and a high metastatic potential in hepatocellular and colorectal carcinomas (Matsumoto et al., 1997; Fujiya et al., 2001; Levy et al., 1997; Levy et al., 1996).

In contrast to these findings, however, Sdc-1 is also a tumor promoter. It supplements Wnt-1 induced tumorigenesis of the mouse mammary gland (Alexander et al., 2000). Enhanced Sdc-1 expression has also been observed in pancreatic (Conejo et al., 2000), gastric (Wiksten et al., 2001) and breast (Burbach et al., 2003; Stanley et al., 1999; Barbareschi et al., 2003) carcinomas and this overexpression correlates with increased tumor aggressiveness and poor clinical prognosis.

Sdc1 is also expressed in vascular endothelial cells. Although its expression is reportedly low in resting cells, it is clearly expressed in endothelial cells undergoing angiogenesis, in activated endothelial cells cultured in vitro, and especially in the blood vessels of tumors (Beauvais et al. 2009).

D. α$_v$β$_3$/α$_v$β$_5$ Integrins and the Insulin-Like Growth Factor Receptor (IGF-1R).

Although classically defined as a vitronectin (VN) receptor, α$_v$β$_3$ is promiscuous and binds many ECM components including fibronectin (FN), fibrinogen, von Willebrand Factor, proteolysed fragments of collagen (COL), laminin (LN), osteopontin, and others (van der Flier and Sonnenberg, 2001). Mechanisms leading to activation of this integrin are complex, including proteolytic cleavage (Ratnikov et al., 2002), conformational changes (affinity modulation), and clustering (avidity modulation; Carman and Springer, 2003). Activation is regulated by "inside-out" signals from the cell interior and is stabilized by ligand interactions that trigger "outside-in" signaling (Giancotti and Ruoslahti, 1999).

The α$_v$β$_3$ integrin is a key regulator of adhesion and signaling in numerous biological processes, including tumor cell migration and metastasis, and angiogenesis. The α$_v$β$_3$ integrin is expressed poorly, if at all, in normal (nontumorigenic) epithelial cells. However, it is expressed and activated in most, if not all, successful carcinomas and carcinoma metastases (Liapis et al., 1996; Felding-Habermann et al., 2001). The activated form of this integrin participates in arrest of tumor cells in the blood stream (Pilch et al., 2002), enhancing their extravasation to target tissues, especially bone, where the activated integrin has further roles in tumor cell proliferation and survival (Brooks et al., 1994; Petitclerc et al., 1999; Eliceiri, 2001).

The αvβ3 integrin is expressed poorly, or not at all, in resting endothelial cells and quiescent blood vessels. But its expression is upregulated in endothelial cells forming new blood vessels where the active integrin is linked not only to adhesion-dependent processes but also to signaling in response to FGF-2 (Eliceiri et al., 1998; Hood et al., 2003) and VEGF. Mice expressing αvβ3 integrin in which Y747/Y759 in its cytoplasmic domain are mutated to prevent its activation show reduced angiogenesis and a failure of VEGF to activate VEGFR2 (Mahabeleshwar et al. 2006, Mahabeleshwar et al. 2007). In the same manner, endothelial cells in vitro show a reduced response to VEGF unless the αvβ3 integrin is engaged by matrix, revealing a cross-talk mechanism between αvβ3 integrin activation and VEGF stimulation of angiogenesis.

The αvβ5 integrin is a close relative of the α$_v$β$_3$ integrin. The αvβ5 integrin is expressed on a variety of tissues and cell types, including endothelia, epithelia and fibroblasts (Felding-Habermann and Cheresh, 1993; Pasqualini et al., 1993). It has a role in matrix adhesion to VN, FN, SPARC and bone sialoprotein (Plow et al., 2000) and is implicated in the invasion of gliomas and metastatic carcinoma cells (Brooks et al., 1997; Jones et al., 1997; Tonn et al., 1998), especially to bone (De et al., 2003). A second major role is in growth factor-induced angiogenesis, where cooperative signaling by the αvβ5 integrin and growth factors regulates endothelial cell proliferation and survival. Like the αvβ3 integrin, αvβ5 expression is upregulated on activated endothelial cells and angiogenesis promoted by VEGF and TGFα in human umbilical vein endothelial cells relies on co-signaling with the αvβ5 integrin (Eliceiri and Cheresh, 1999; Friedlander et al., 1995).

The insulin-like growth factor-1 receptor (IGF-1R) is a member of the insulin receptor family of growth factor receptors, and is activated by IGF-1. Like the insulin-receptor, the cytoplasmic domain of the activated receptor binds a number of signaling effectors such as insulin-receptor substrates-1 and -2 (IRS-1, IRS-2), activating MAPK signaling pathways, Akt and others (Baserga et al. 1997, Chitnis et al. 2008). It has a prominent role in cell and organ growth, tumorigenesis and angiogenesis. IGF-1R is upregulated or hyperactivated in a number of carcinomas, and carcinomas treated with chemotherapeutic drugs against other receptor tyrosine kinases such as EGFR develop resistance due to upregulation of IGF-1R activity (Lu et al. 2001). Among its other activities, it is known to engage and suppress the activation of apoptosis signal-regulating kinase-1 (ASK-1), which allows cells to suppress apoptotsis (Galvan et al. 2003, Hayakawa et al. 2006). This potentially explains why IGF-1R is upregulated in tumors in which genotoxic and metabolic stress can promote apoptosis and death of the tumor cell. Suppression of ASK-1 has a prominent role in multiple myeloma, a disease arising from malignant plasma cells that express high levels of Sdc1 (CD138) (Lin et al. 2012). Plasma cells express high levels of immunoglobulins. This generates endoplasmic reticulum stress due to the accumulation of unfolded or mis-assembled proteins. This stress activates the unfolded protein response (UPR) to upregulate the expression of chaperone proteins to aid proper protein folding and assembly. Failure to resolve the ER stress causes activation of ASK-1 and apoptosis. The plasma cells avoid apoptosis by expressing the transcription factor Blimp-1, which suppresses ASK-1 expression (Lin et al. 2012). Malignant plasma cells (myeloma cells) maintain this suppression to avoid apoptosis not only due to their continued high expression of immunoglobulins, but also due to genotoxic and metabolic stress arising from their transformed phenotype. Work from the inventors' laboratory has shown that suppression of ASK-1 activation in myeloma, other tumor cells and activated endothelial cells relies on IGF1R and its coupling to Sdc1 and $\alpha v\beta 3$ or $\alpha v\beta 5$ integrin (Beauvais et al., 2016. This is prevented by a peptide therapeutic, $SSTN_{IGF1R}$ (see FIG. 2), leading to cell death (Beauvais et al., 2016). This publication also reports that $SSTN_{IGF1R}$ has remarkable stability when incubated in plasma, which normally leads to the rapid destruction of peptides via exoprotease activity. This extends in vivo as well, where the peptide has a half-life of ca. 27 hr. (Beauvais et al., 2016), compared to most peptides that are destroyed or cleared from the circulation within minutes.

E. VLA-4 (Very Late Antigen-4; the $\alpha 4\beta 1$ Integrin)

VLA-4 is an integrin that is expressed on lymphoid and myeloid leukocytes (e.g., B-cells, T-cells, monocytes and macrophages, granulocytes) and facilitates their adhesion to endothelial cells and the ECM during extravasation from the blood stream (Yusuf-Makagiansar et al. 2002). This is a highly regulated process in which leukocytes responding to chemokines attach to the endothelial lining of blood vessels, roll to a stop via selectin-mediated adhesion, then activate VLA-4 and LFA-1 (leukocyte functional antigen-1, e.g., the $\alpha L\beta 2$ integrin), which rapidly engage their ligands (vascular cell adhesion molecule-1 (VCAM-1) and intercellular cell adhesion molecule-1 (ICAM-1)) on the endothelial cells to stabilize the adhesion. The leukocytes then invade through the endothelium to the underlying tissue utilizing these integrins.

The polarized migration of leukocytes during their extravasation from the blood, or endothelial cells during angiogenesis or in response to blood flow, is dependent on two different activity states of VLA-4. Basal activation of the integrin achieves adhesion necessary for migration of the cells. But a second activation event, namely phosphorylation of serine 988 in the alpha subunit, causes the integrin to polarize to the leading edge of the cell and actively carry out invasive migration. This latter step involves activation of Rac-1 to generate actively ruffling lamellipodia (Han et al. 2001, Han et al. 2003, Nishiya et al. 2005, Goldfinger et al. 2008). Activation of Rac1 depends on VLA-4 phosphorylation on serine 988 (S988) in the cytoplasmic domain of the $\alpha 4$ integrin subunit by PKA, which somehow acts on VLA-4 only at the leading edge. Note that basally activated VLA-4 is also engaged in active cell-matrix adhesion signaling elsewhere on the cells, but its activation of Rac1 and generation of an active lamellipodium is restricted to the leading edge due to activation of PKA specifically at this site. Importantly, the extravasation of B- and T-lymphocytes, which in many instances relies on a different integrin (LFA-1, the $\alpha L\beta 2$ integrin), nonetheless relies on VLA-4 as well because LFA-1 depends on cross-talk with VLA-4 to be activated (Cantor et al. 2015). Thus, targeting VLA-4 activation has significant impact on leukocyte and lymphoma invasion.

Targeting this mechanism is likely to be critical for diseases as disparate as multiple sclerosis, atherosclerosis and tumorigenesis. In multiple sclerosis, VLA-4 is essential for the processes by which T-cells gain access to the brain by helping the cells to penetrate the blood-brain barrier that normally restricts immune cell access. An approach used clinically to prevent this autoimmune disorder has been to block the action of VLA-4 so that reactive T-cells are unable to enter the brain and thus unable to attack the myelin sheath of nerve axons. Similar approaches would be useful in other autoimmune diseases, such as diabetes, Chrohn's disease and ciliac disease, to name a few. The VLA-4 blocking antibody Natalizumab is an FDA-approved therapeutic for use against VLA-4 in autoimmune diseases, and is in use against multiple sclerosis and Crohn's disease (Millard et al. 2011). But, natalizumab treatment is sometimes accompanied by progressive multifocal leukoencephalopathy (PML), a demvrelinating disease of the CNS caused by the JC polyoma virus, and a disease mainly seen in highly inmunocompromised patients (Millard et al. 2011).

In ateroslerosis, monocytes expressing VLA-4 are attracted to damaged blood vessels (preatherosclerosis) due to upregulation of P-selectin and VCAM-1 on the vessels by inflammatory cytokines, to which the monocytes bind via the VLA-4 integrin. The monocytes then migrate into the subendothelial space and differentiate into foam cells (a form of macrophage) that are a central cause of atherosclerosis (Mestas and Ley 2008).

VLA-4 has many roles in tumorigenesis. Certain tumors, especially melanoma, lymphomas, leukemias and multiple myeloma, express VLA-4 and rely on it for invasion and survival. Other types of tumors show sporadic expression, and their susceptibility to a VLA-4 blocking drug would best be determined by an examining its expression as one of the tumor biomarkers. When expressed, the integrin plays a role in the adhesion and invasion of the cells, including extravasation from the blood stream to sites of metastatic tumorigenesis by interacting with VCAM-1 on vascular or lymphatic endothelial cells. When the tumor microenvironment is rich in VLA-4 ligands, such as in tumors that metastasize to the bone marrow that is rich in fibronectin and VCAM-1, VLA-4 engaged to these ligands provides further support to the tumor by initiating signaling leading to "cell adhesion-mediated drug resistance" or CAM-DR" that suppresses cell killing by cancer drugs. Thus, the ability to rationally regulate VLA-4 activation that may depend on Sdc1 using a peptide that targets this mechanism will be highly useful for treating tumor cell invasion and resistance to therapeutics.

Leukocytes and monocytes also play a major role in tumorigenesis. Monocytes infiltrate to the tumor microenvironment, differentiate into type 2 macrophages, and release cytokines that support tumor growth. This contrasts with NK and T-cells that can have beneficial roles by targeting and causing the destruction of tumors. However, the relative roles of VLA-4 and LFA-1 in this mechanism remain largely unknown.

VLA-4 is also expressed on vascular and lymphatic endothelial cells undergoing angiogenesis, where it is more commonly referred to as the α4β1 integrin (Gingis-Velitski et al. 2004, Garmy-Susini et al. 2005, Garmy-Susini et al. 2010). VLA-4 expression is particularly prominent in tumor-induced angiogenesis, and its inhibition using blocking antibodies disrupts both tumor growth and the metastatic spread of tumor cells that relies on blood and lymph vessels as migratory routes for their dissemination.

VLA-4 has now been shown by the inventors to depend on an interaction between its extracellular domain and the extracellular domain of Sdc1 (Jung et al., 2016). This depends on the DFTF motif (aa210-214) in human Sdc1. Integrin activation on myeloma, endothelial, melanoma and T-lymphoma cells, defined by monitoring the adhesion to VLA-4 ligands, is prevented by SSTN$_{VLA4}$, by silencing the expression of Sdc1, or by deleting the DFTF motif from Sdc1 (Jung et al., 2016 and figures accompanying this application). Thus, the peptide SSTN$_{VLA4}$, or a novel peptide designed to include the SSTN$_{VLA4}$ sequence, is predicted to block the many VLA-4 activities upon which immune, endothelial and tumor cells depend.

SUMMARY

We disclose herein syndecan-1 fusion peptides that demonstrate significant bioactivity against cancer cells, immune cells and endothelial cells. The disclosed fusion peptides include (1) an IGF-1R-binding segment consisting of the sequence of amino acids 93-119 of human Sdc1, having the sequence LPAGEGPKEGEAVVLPEVEPGLTAREQ (SEQ ID NO: 1); and (2) a VLA-4-binding segment consisting of the sequence of amino acids 210-221 of human Sdc1, having the sequence DFTFETSGENTA (SEQ ID NO:2). Notably, although we had previously shown that the deletion of glutamate (E) at position 120 of Sdc1 dramatically reduces the bioactivity of the IGF-1R-binding segment alone, this amino acid does not need to be included in the IGF-1R-binding segment of the bioactive fusion peptides.

In a non-limiting example, the fusion peptide includes a larger segment consisting of the IGF-1R and VLA-4-binding segments sequentially linked together, thus having the sequence: LPAGEGPKEGEAVVLPEVEPGLTAREQDFTFETSGENTA (SEQ ID NO:3).

The disclosed fusion peptides are not naturally occurring, in that the sequence of the amino acid segment that is interposed between the IGF-1R-binding segment and the VLA-4-binding segment, if any, is different than the sequence of amino acids 120-209 of human Sdc1.

In a first aspect, the disclosure encompasses a fusion peptide of from 39 to 100 amino acid residues in length. The fusion peptide includes (a) an IGF-1R-binding segment made up of the amino acid sequence of residues 93-119 of human Sdc1 (SEQ ID NO:1), and (b) a VLA-4-binding segment made up of the amino acid sequence of residues 210-221 of human Sdc1 (SEQ ID NO:2).

In some embodiments, the fusion peptide is 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 or 100 amino acid residues in length.

In some embodiments, the fusion peptide is from 39 to 90 amino acid residues in length. In some such embodiments, the fusion peptide is from 39 to 80 amino acid residues in length. In some such embodiments, the fusion peptide is from 39 to 70 amino acid residues in length. In some such embodiments, the fusion peptide is from 39 to 65 amino acid residues in length. In some such embodiments, the fusion peptide is from 39 to 60 amino acid residues in length.

In some embodiments, the fusion peptide consists essentially of the IGF-1R-binding segment and the VLA-4-binding segment (i.e., has no other components affecting the activity of the fusion peptide). In some such embodiments, the fusion peptide consists of the IGF-1R-binding segment and the VLA-4-binding segment (i.e., has no other components).

In some embodiments, the fusion peptide includes a segment made up of the IGF-1R-binding segment (SEQ ID NO:1) and the VLA-4-binding segment (SEQ ID NO:2) fused directly together (SEQ ID NO:3). In some such embodiments, the fusion peptide consists essentially of SEQ ID NO:3 (i.e., has no other components affecting the activity of the fusion peptide). In some such embodiments, the fusion peptide consists of SEQ ID NO:3 (i.e., has no other components).

In some embodiments, the fusion peptide includes a linker that is interposed between the IGF-1R-binding segment and the VLA-4-binding segment. In some such embodiments, the fusion peptide consists essentially of the IGF-1R-binding segment, the VLA-4-binding segment, and the linker (i.e., has no other components affecting the activity of the fusion peptide). In some such embodiments, the fusion peptide consists of the IGF-1R-binding segment, the VLA-4-binding segment, and the linker (i.e., has no other components).

In some embodiments, the linker includes a glutamate residue (E) attached directly to the C-terminus (Q residue) of the IGF-1R-binding segment. In some such embodiments, the linker consists of the glutamate residue.

In some embodiments, the linker includes one or more alanine (A) residues. In some such embodiments, the linker includes the amino acid sequence AAAA (SEQ ID NO:4). In some such embodiments, the linker consists essentially of the amino acid sequence AAAA (SEQ ID NO:4) or the amino acid sequence EAAAA (SEQ ID NO:5). In some such embodiments, the linker consists of the amino acid sequence AAAA (SEQ ID NO:4) or the amino acid sequence EAAAA (SEQ ID NO:5).

In a second aspect, the disclosure encompasses a nucleic acid segment that encodes any of the fusion peptides as described above.

In a third aspect, the disclosure encompasses a pharmaceutical composition that includes (a) any of the fusion peptides as described above, and (b) a pharmaceutically acceptable buffer, diluent or excipient.

In a fourth aspect, the disclosure encompasses a method of inhibiting interaction of syndecan 1 with VLA-4 and/or IGF-1R. The method includes the step of contacting a cell expressing VLA-4 and/or IGF-1R with a fusion peptide as described above, whereby the interaction of syndecan 1 with VLA-4 and/or IGF-1R is inhibited.

In some embodiments, the cell is a cancer cell. In some such embodiments, the method facilitates the death of the cancer cell. In some such embodiments, the method stimulates T-cell homing to the cancer cell.

In some embodiments, the cancer cell is a carcinoma, a myeloma, a melanoma or a glioma.

In some embodiments, the method also includes the step of treating the cancer cell with a second cancer therapy. Non-limiting examples of second cancer therapies that could be used include radiation, chemotherapy, hormonal therapy, toxin therapy, or immunotherapy.

In some embodiments, the cancer cell is a metastatic cancer cell, a recurrent cancer cell or a multiply drug resistant cancer cell. In some embodiments, the cancer cell is a breast cancer cell, a myeloma cancer cell, a glioma cell, a melanoma cell, a prostate cancer cell, or an ovarian cancer cell, In some embodiments, the cell is an immune cell. In some such embodiments, the immune cell is a leukocyte. In some such embodiments, the immune cell is a lymphocyte, such as a T-cell. In some such embodiments, the method stimulates T-cell homing to a second cell type, such as a cancer cell.

In some embodiments, the method further includes treating the immune cell with an immunosuppressive therapy, such as a steroid.

In a fifth aspect, the disclosure encompasses a method of treating a subject with a cancer, the cells of which express VLA-4 and/or IGF-1R. The method includes the step of contacting one or more of the cells with a fusion peptide as described above, whereby the cancer is effectively treated.

In some embodiments, the subject is a mammal. In some such embodiments, the mammal is a domesticated mammal, such as a dog. In other such embodiments, the mammal is a human.

In some embodiments, the cancer cell is a carcinoma, a myeloma, a melanoma or a glioma.

In some embodiments, the fusion peptide is administered directly to the cancer cell, locally to the cancer cells, regionally to the cancer cells, or systemically.

In some embodiments, the method further includes the step of administering to the subject a second cancer therapy, including, without limitation, chemotherapy, radiotherapy, immunotherapy, hormonal therapy, toxin therapy, surgery, or combinations thereof.

In some embodiments, the cancer cell is a metastatic cancer cell, a recurrent cancer cell or a multiply drug resistant cancer cell.

In some embodiments, the cancer cell is a breast cancer cell, a myeloma cancer cell, a glioma cell, a melanoma cell, prostate cancer cell, an ovarian cancer cell, In some embodiments, the fusion peptide is administered intravenously, intra-arterially, subcutaneously, intratumorally, topically, or orally.

In some embodiments, the fusion peptide is administered locally to a tumor, regionally to a tumor, or systemically.

In some embodiments, the fusion peptide facilitates the death of the cancer cells. In some embodiments, the fusion peptide stimulates T-cell homing and killing of the cancer cells.

In a sixth aspect, the disclosure encompasses a method of inhibiting an autoimmune disease in a subject. The method includes the step of administering to the subject a fusion peptide as described above.

In some embodiments, the subject is a mammal. In some such embodiments, the mammal is a domesticated mammal, such as a dog. In other such embodiments, the mammal is a human.

In some embodiments, the autoimmune disease is rheumatoid arthritis, systemic lupus erythematous, Sjogrens's disease, Crohn's disease, ulcerative colitis, psoratic arthritis, multiple sclerosis or ankylosing spondylitis.

In some embodiments, the fusion peptide is administered intravenously, intra-arterially, subcutaneously, topically, intra-articularly or orally.

In some embodiments, the method further includes the step of administering to the subject a second autoimmune therapy, such as administering a steroid.

In a seventh aspect, the disclosure encompasses a fusion peptide as described above, for use in treating cancer.

In an eight aspect, the disclosure encompasses a fusion peptide as described above, for use in treating an autoimmune disease.

In a ninth aspect, the disclosure encompasses a fusion peptide as described above, for use in manufacturing a medicament for treating cancer.

In a tenth aspect, the disclosure encompasses a fusion peptide as described above, for use in manufacturing a medicament for treating an autoimmune disease.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number. It is contemplated that any method or composition described herein can be implemented with respect to any other method or composition described herein.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description.

FIG. 3. MINIMAL FUNCTIONAL SIZE FOR $SSTN_{IGF1R}$. A peptide comprising amino acids 88-119 in mouse or 89-120 in human syndecan was initially shown to retain full inhibitory activity (Beauvais et al., 2009). Work in the inventor's laboratory now demonstrates that the minimal functional size of the human peptide is amino acids 93-120 (92-119 in mouse). Removal of leucine (L) at position 93, or the glutamate (E) residue at position 120 reduces activity by 70-80% and removal of additional amino acids further reduces or abolishes activity based on use of peptides in endothelial cell adhesion or myeloma cell survival assays. (*Data extrapolated from truncation of mouse peptide as shown in Beauvais et al., 2009). Note that myeloma cells are less sensitive to truncation of $SSTN_{IGF1R}$ at the N-terminus and that the peptide in with leucine and proline at positions 93 and 94 retains ca. 30% activity of these cells, whereas endothelial cells and other tumors cells are not affected by this peptide (Beauvais et al., 2016). From top to bottom, the seven amino acid sequences shown in FIG. 3 are SEQ ID NO:7, SEQ ID NO:1, SEQ ID NO:8, SEQ ID NO:9, SEQ ID NO:10, SEQ ID NO:11, and SEQ ID NO:6.

FIG. 12. MINIMAL FUNCTIONAL SIZE OF $SSTN_{VLA4}$. Deletion of the N-terminal DFTF motif abolishes peptide inhibitory activity, demonstrating the importance of the N-terminal amino acids. From top to bottom, the seven listed sequences are SEQ ID NO:16, SEQ ID NO:15, SEQ ID NO:12, SEQ ID NO:14, SEQ ID NO:17, SEQ ID NO:2, and SEQ ID NO:2.

FIGS. 13A, 13B, 13C AND 13D. DERIVATION OF NEW MASTER INHIBITORY $SSTN_{I/V}$. 13A. Model depicting $SSTN_{IGF1R}$ and $SSTN_{VLA4}$. Schematic showing the sites in the Sdc1 extracellular domain that give rise to the $SSTN_{IGF1R}$ and $SSTN_{VLA4}$ peptides and their respective activities. 13B. Shows duplicated acidic motif in Sdc1. The identification of an acidic motif that is present at the C-terminus of the $SSTN_{IGF1R}$ peptide and also present in the amino acid sequence of Sdc1 just upstream and within the N-terminus of the $SSTN_{VLA4}$ peptide. The top line (human) sequences are SEQ ID NO:18 (left) and SEQ ID NO:19 (right). The second from the top line (mouse) sequences are SEQ ID NO:20 (left) and SEQ ID NO:19 (right). The third from the top line (rat) sequences are SEQ ID NO:21 (left) and SEQ ID NO:19 (right). The fourth from the top line (macaque) sequences are SEQ ID NO:22 (left) and SEQ ID NO:19 (right). The fifth from the top line (gibbon) sequences are SEQ ID NO:23 (left) and SEQ ID NO:19 (right). The sixth from the top line (hamster) sequences are SEQ ID NO:24 (left) and SEQ ID NO:19 (right). The bottom line (orca) sequences are SEQ ID NO:25 (left) and SEQ ID NO:19 (right). 13C. Shows the creation of a novel combination therapeutic peptide. Schematic showing the fusion of $SSTN_{VLA4}$ and $SSTN_{IGF1R}$, using the overlapping "EQE" motif present in $SSTN_{IGF1R}$ and present just upstream of $SSTN_{VLA4}$ in the native Sdc1 sequence, giving rise to a novel combination therapeutic ($SSTN_{I/V}$) predicted to share the inhibitory properties of both inhibitors. Using myeloma as an example, from top to bottom, the three sequences shown are SEQ ID NO:6, SEQ ID NO:26, and SEQ ID NO:3. $SSTN_{I/V}$ is predicted to be highly effective against myeloma cell survival and invasion, as well as endothelial cell-mediated angiogenesis required by the tumor. As summarized in subsequent FIGS. 13D-17, $SSTN_{I/V}$ is equally as effective as $SSTN_{IGF1R}$ in killing myeloma cells, and equally as effective as $SSTN_{VLA4}$ in blocking VLA-4-mediated adhesion, and displays the same remarkable stability as both $SSTN_{IGF1R}$ and $SSTN_{VLA4}$. 13D. Illustrates the peptides tested for inhibitory activity against VLA-4 activation. From top to bottom, the five sequences shown are SEQ ID NO:27, SEQ ID NO:28, SEQ ID NO:29, SEQ ID NO:30, and SEQ ID NO:3. Joining of $SSTN_{IGF1R}$ and $SSTN_{VLA4}$ via the shared acidic amino acid motif, despite truncation of the essential glutamate (E) is as effective as joining $SSTN_{IGF1R}$ and $SSTN_{VLA4}$ together using a polyalanine (AAAA, SEQ ID NO:4) spacer.

DETAILED DESCRIPTION

Figure 1:
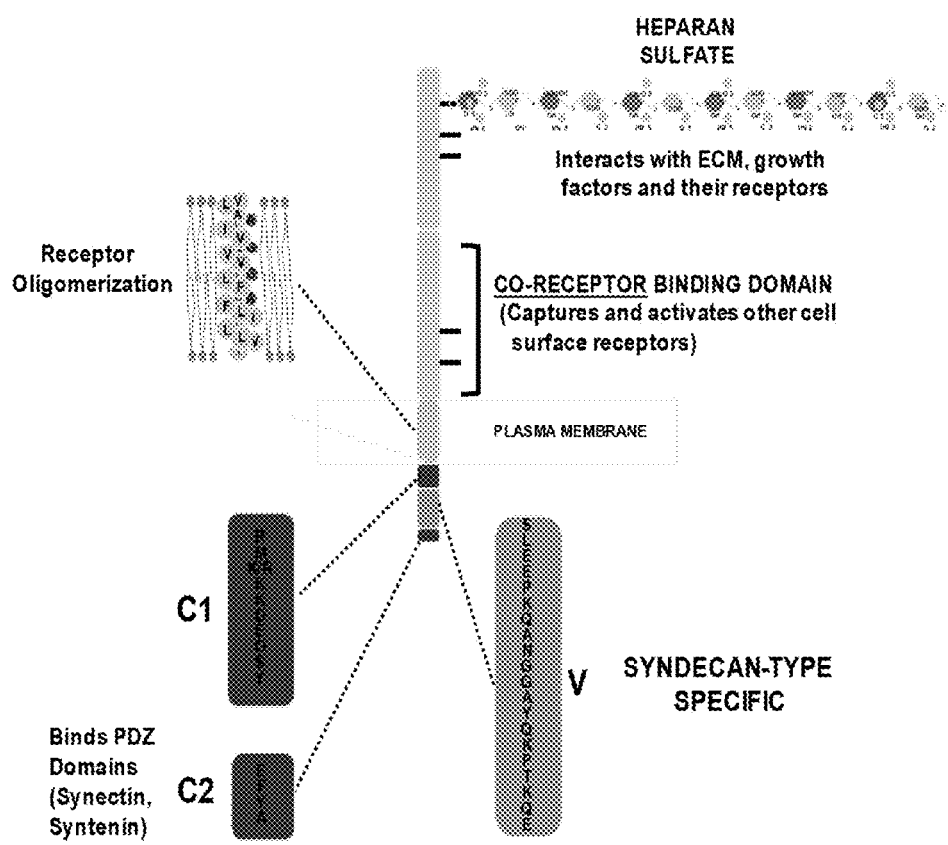
FIG. 1. MODEL OF THE SYNDECAN FUNCTIONAL DOMAINS. Shown are the heparan sulfate glycosaminoglycan chains that bind the matrix as well as heparin-binding growth factors. The transmembrane domain contains a repeating glycine/alanine motif, in addition to specific interacting amino acids, that promote syndecan dimerization in the plane of the plasma membrane. Vertical top to bottom amino sequences shown in the receptor oligomerization schematic at the upper left are, from left to right, SEQ ID NO:32 (LIVLFL), SEQ ID NO:33 (VAVVFLL) and SEQ ID NO:34 (AGGAIV). The cytoplasmic domain consists of exactly conserved C1 (RMKKKDEGSY, SEQ ID NO:35; or RMRKKDEGSY, SEQ ID NO:36) and C2 (EFYA, SEQ ID NO:37) domains interspersed with a variable (V) domain that is specific to each of the four family members (the example variable domain sequence shown in the figure, SLEEPKQANGGAYQKPTKQE, is SEQ ID NO:38). The extracellular domain contains a "co-receptor" binding domain that captures and organizes other cell surface receptors into signaling complexes.
Figure 2:
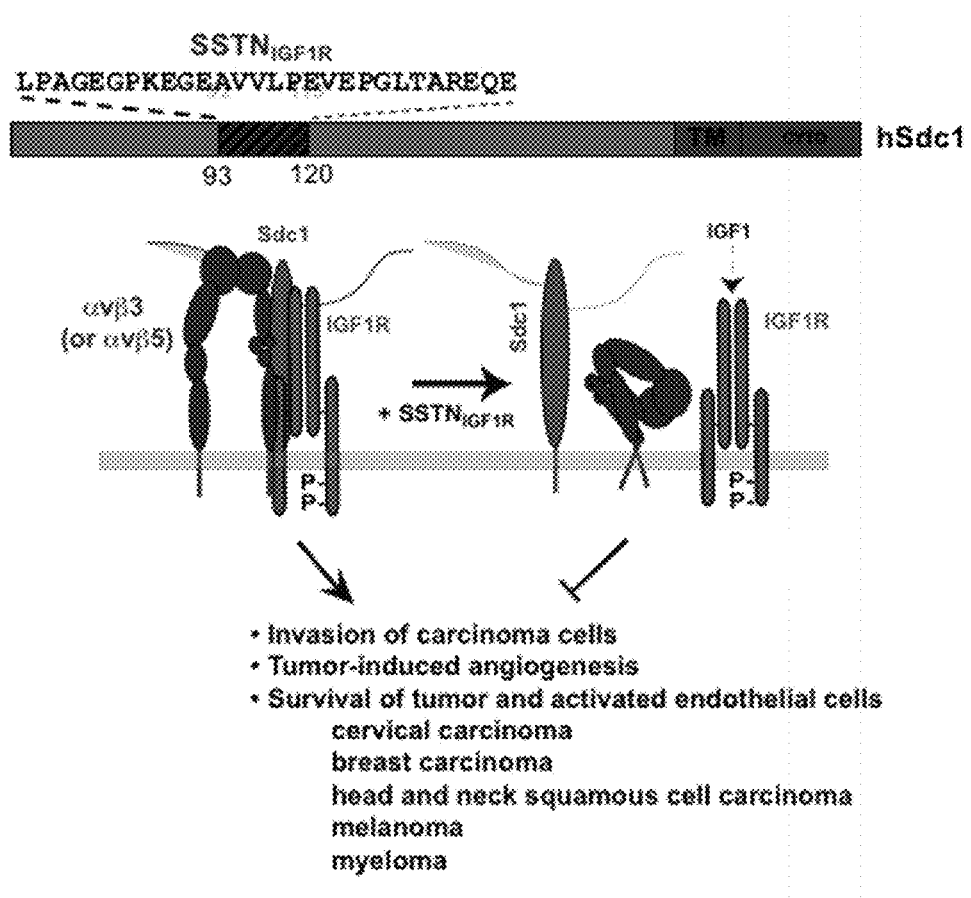
FIG. 2. THE SYNDECAN-1 (SDC1)-COUPLED IGF-1R COMPLEX AND ITS INHIBITORY SYNSTATIN (SSTN$_{IGF1R}$). Sdc1 captures the αvβ3 or αvβ5 integrin to a docking site in its extracellular domain (SEQ ID NO:6, aa93-120 in human Sdc1, second line of FIG. 2). The Sdc1 and integrin together provide a docking site that captures the IGF-1R. This activates IGF-1R independent of IGF-1 and IGF-1R signaling causes activation of the integrin. A peptide mimetic of the docking site ($SSTN_{IGF1R}$) displaces the integrin and IGF-1R, inactivating the integrin and disrupting IGF-1R signaling that is necessary for tumor cell survival and angiogenesis, even in the presence of IGF-1.

The inventors have now clearly shown that the αvβ3 integrin and the homologous αvβ5 integrin directly engage the extracellular domain of Sdc1 (aa93-120) when expressed on tumor cells and vascular endothelial cells. This site in Sdc1, together with the bound integrin, provide a docking face to which the IGF-1R binds (Beauvais et al. 2009, Beauvais and Rapraeger 2010, Rapraeger 2013) (FIG. 2). IGF-1R is activated when captured by the Sdc1/integrin pair and this activation does not require IGF-1 ligand. Because docking of IGF-1R to Sdc1 requires the $\alpha v\beta 3$ or $\alpha v\beta 5$ integrin, activation of IGF-1R by this mechanism occurs only on cells that express Sdc1 and one of the integrins, largely tumor cells and activated endothelial cells undergoing pathological angiogenesis. The receptor complex is not expressed in normal or resting cells because the integrin is not present. This ternary receptor complex has a role in the migration of cells that express it, as well as their survival. In vascular endothelial cells, activation of IGF-1R during angiogenesis depends on homotypic cell-cell interactions mediated by VE-cadherin between endothelial cells as they migrate. Blockade of VE-cadherin with blocking antibodies has been shown previously to block angiogenesis. The inventors have shown that the activation of IGF-1R downstream of VE-cadherin homotypic adhesion depends on coupling of IGF-1R to Sdc1 and the $\alpha v\beta 3$ integrin. In turn, active IGF-1R is required for VEGF to stimulate the activation of VEGFR2 that is necessary for angiogenesis.

I. $SSTN_{IGF1R}$

SSTN-IGF-1R ($SSTN_{IGF1R}$) is a syndecan-1-derived peptide mimicking the site in the extracellular domain of syndecan-1 (Sdc1) that captures IGF-1R and the $\alpha v\beta 3$ or $\alpha v\beta 5$ integrin (FIG. 2). The inventors have now shown that the shortest peptide that retains full activity consists of amino acids 93-120 in human Sdc1 (hSdc1) (FIG. 3). Removal of either the Leucine (L) in position 93, or truncation of the glutamate (E) at position 120 dramatically reduces the activity of the peptide and further truncation abolishes activity altogether. This demonstrates that these two amino acids, and their orientation or exposure in the peptide is critical for its inhibitory function.

The inventors have shown conclusively that $SSTN_{IGF1R}$ blocks tumor cell migration, blocks tumor growth in vivo and blocks angiogenesis. It does so by targeting the Sdc1-coupled ternary complex on both activated endothelial cells and on the tumor cells. Its effect on angiogenesis occurs early in the angiogenesis process, a stage at which VE-cadherin-mediated adhesion between adjacent endothelial cells activates the ternary complex, which is necessary for VEGF signaling through VEGFR2 (Rapraeger, 2013). How this works is not yet clear. Later stages of angiogenesis, which also depend on VEGFR2, are not affected by $SSTN_{IGF1R}$, indicating that is it highly specific for this mechanism. It is highly effective in vivo, where it has been shown to block abnormal angiogenesis induced by FGF in the mouse cornea as well as tumor-induced angiogenesis (Beauvais et al., 2009). $SSTN_{IGF1R}$, unlike most peptides that fail in the clinic because of their instability and rapid clearance in vivo, is remarkably stable, resisting degradation in serum that destroys most peptides and showing long half-life in vivo (Beauvais et al., 2016)

Figure 4A:
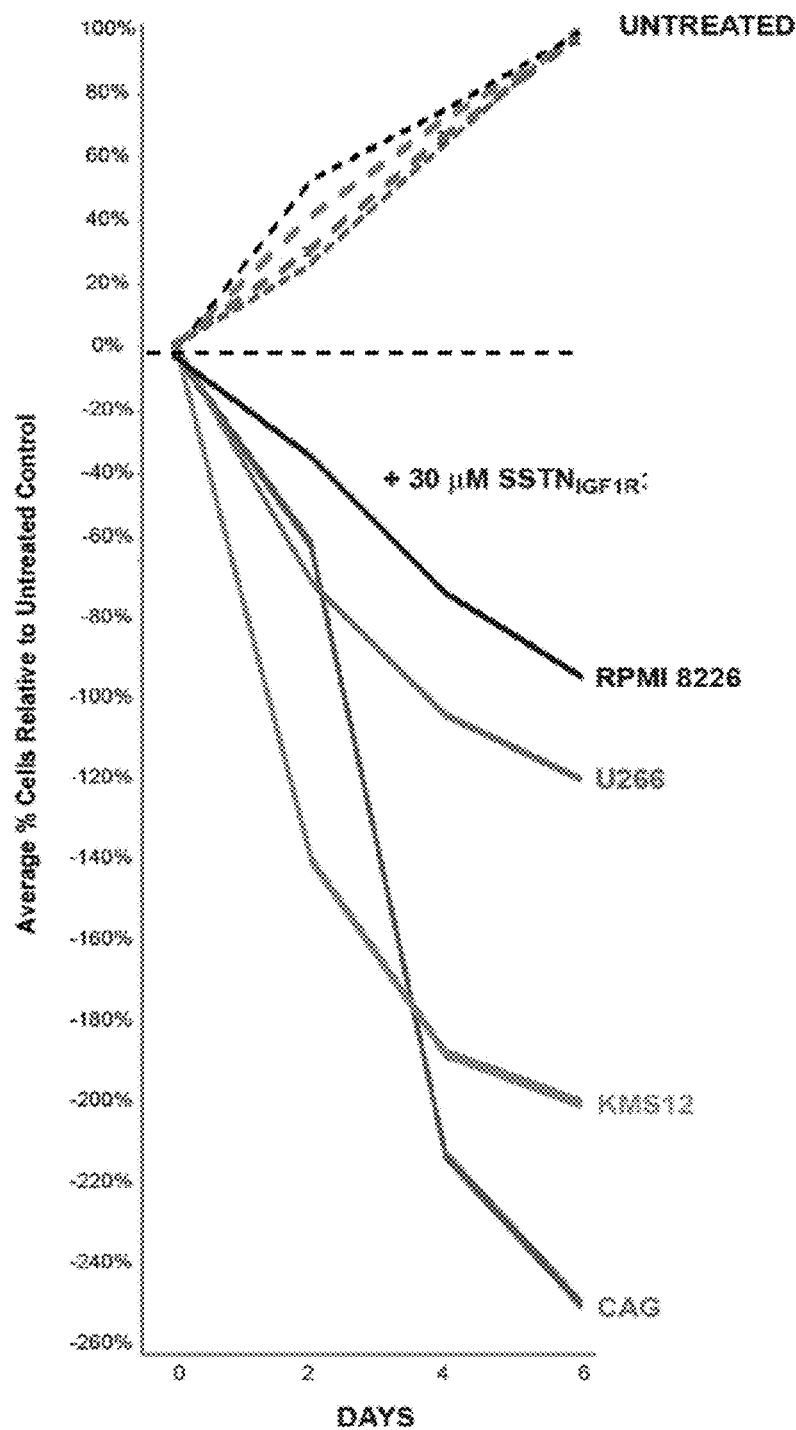
FIGS. 4A and 4B. SSTN INHIBITS GROWTH OF MYELOMA TUMORS. 4A. Graph showing results for SSTN-treated myeloma cell lines. Myeloma cell growth in complete culture medium containing 30 µM $SSTN_{IGF1R}$ is quantified over 3 days and graphed as % increase in cell number relative to untreated cells (set to 100%); 4B. Results shown for SSTN-treated CAG myeloma tumor xenografts in mice. CAG myeloma cells implanted subcutaneously in immunodeficient nude (nu/nu) mice were allowed to form palpable tumors for 7-10 days. Mice were then implanted with Alzet pumps delivering 0.365 mg/kg/day of $SSTN_{IGF1R}$, or saline as a control, for an additional 4 weeks. Shown are tumors harvested at the end of the 4-week treatment period (18 per cohort shown; 'X' denotes no tumor found). (Modified from (Beauvais et al. 2016)).
Figure 4B:
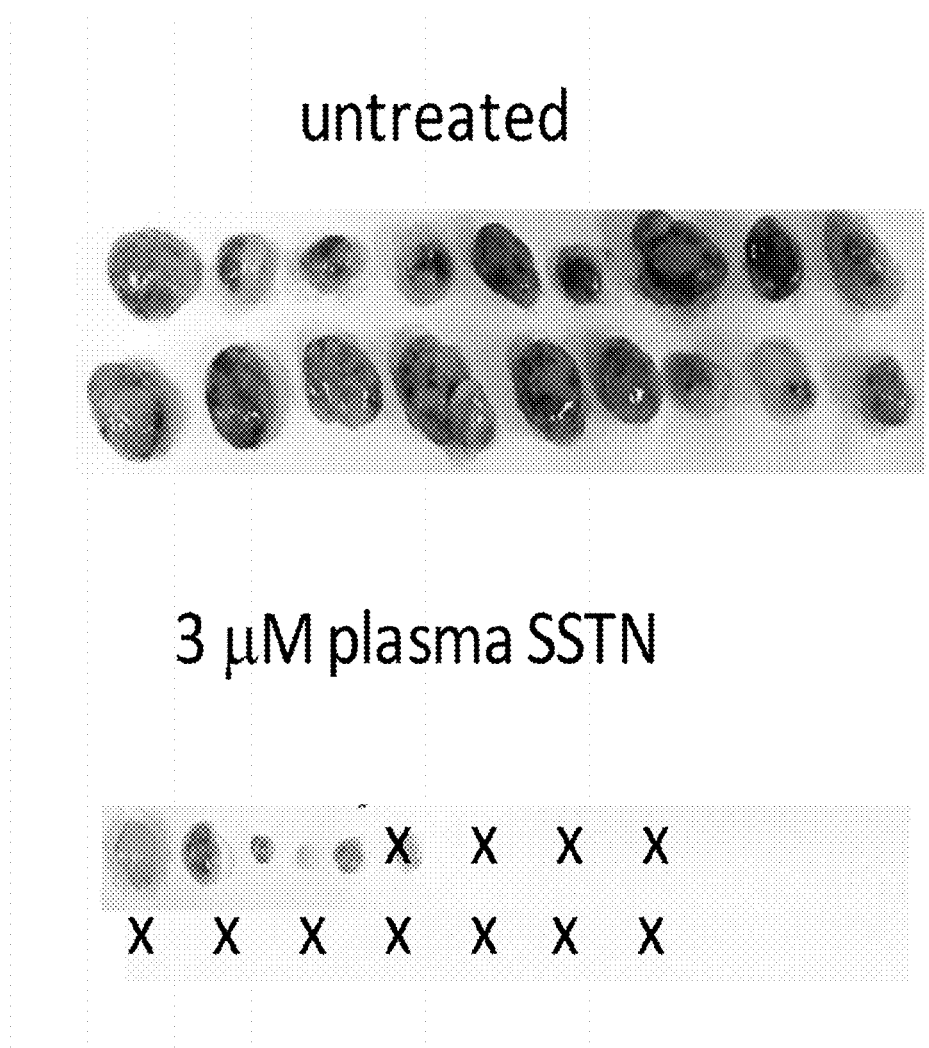
Figure 5:
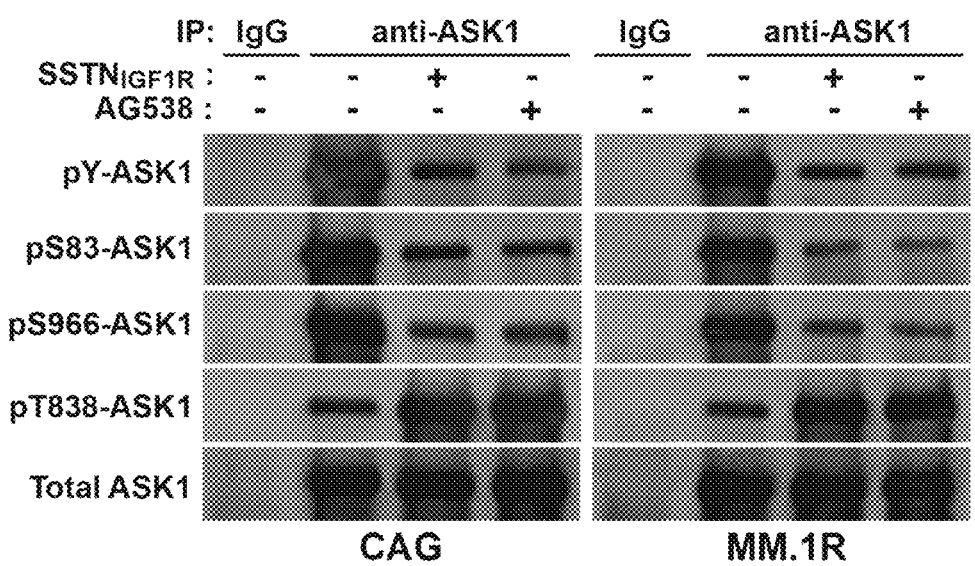
FIG. 5. $SSTN_{IGF1R}$ ACTIVATES ASK-1 IN MYELOMA. Apoptosis signal regulating kinase-1 (ASK1) is immunoprecipitated from CAG or MM.1R myeloma cells treated for 6 hr with 10 µM $SSTN_{IGF1R}$ or 10 µM IGF-1R inhibitor AG538 and probed for inactive (pY, pSer83 and pSer966), active (pThr838) or total ASK1. (Modified from (Beauvais et al. 2016)).
Figure 6A:
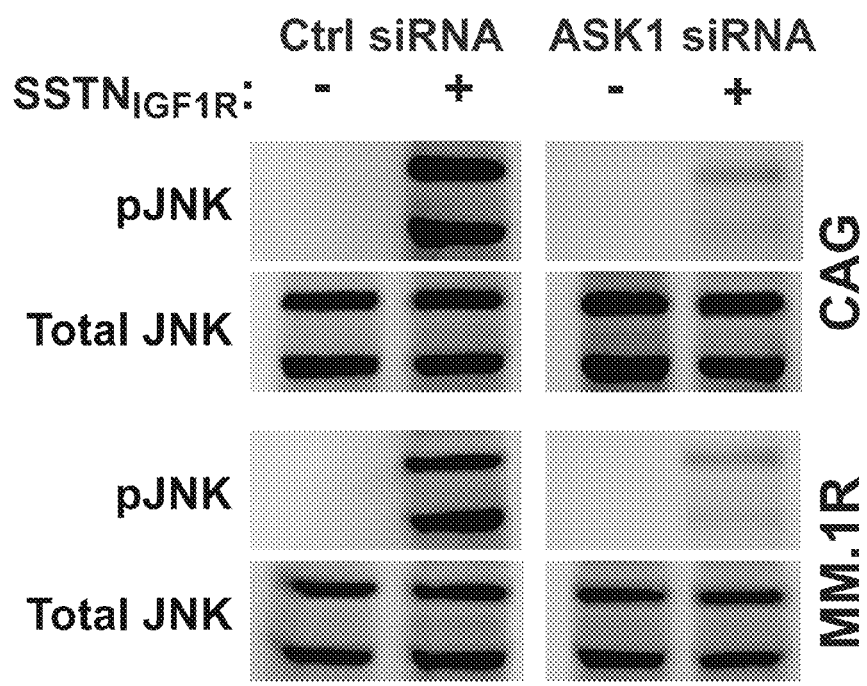
FIGS. 6A, 6B and 6C. SILENCING ASK-1 EXPRESSION PREVENTS JNK ACTIVATION AND APOPTOSIS IN MYELOMA CELLS TREATED WITH $SSTN_{IGF1R}$. 6A. Equal cell equivalents from control or ASK1 siRNA-transfected CAG and MM.1R myeloma cells (48 hr post-transfection) treated with or without 30 µM $SSTN_{IGF1R}$ for 8 hr are analyzed for levels of active JNK (pThr183/pTyr185) and total JNK; 6B. Active Caspase 3/7 is quantified in control or ASK1 siRNA-transfected CAG and MM.1R cells treated as in (6A). Model (6C) depicts capture of inactive αvβ5 integrin and IGF-1R via the docking site in the extracellular domain of Sdc1, which causes autophosphorylation of IGF-1R and binding of inactive ASK1 (with inactivating phosphorylation on Ser83, Ser966 (S) and tyrosines (Y)). Displacement of the integrin and IGF-1R from Sdc1 inactivates IGF-1R, allow ASK1 activation via autophosphorylation of Thr838 (T), and downstream activation of JNK via MKK4 or MKK7, leading to caspase activation and apoptosis. (Modified from (Beauvais et al. 2016).
Figure 6B:
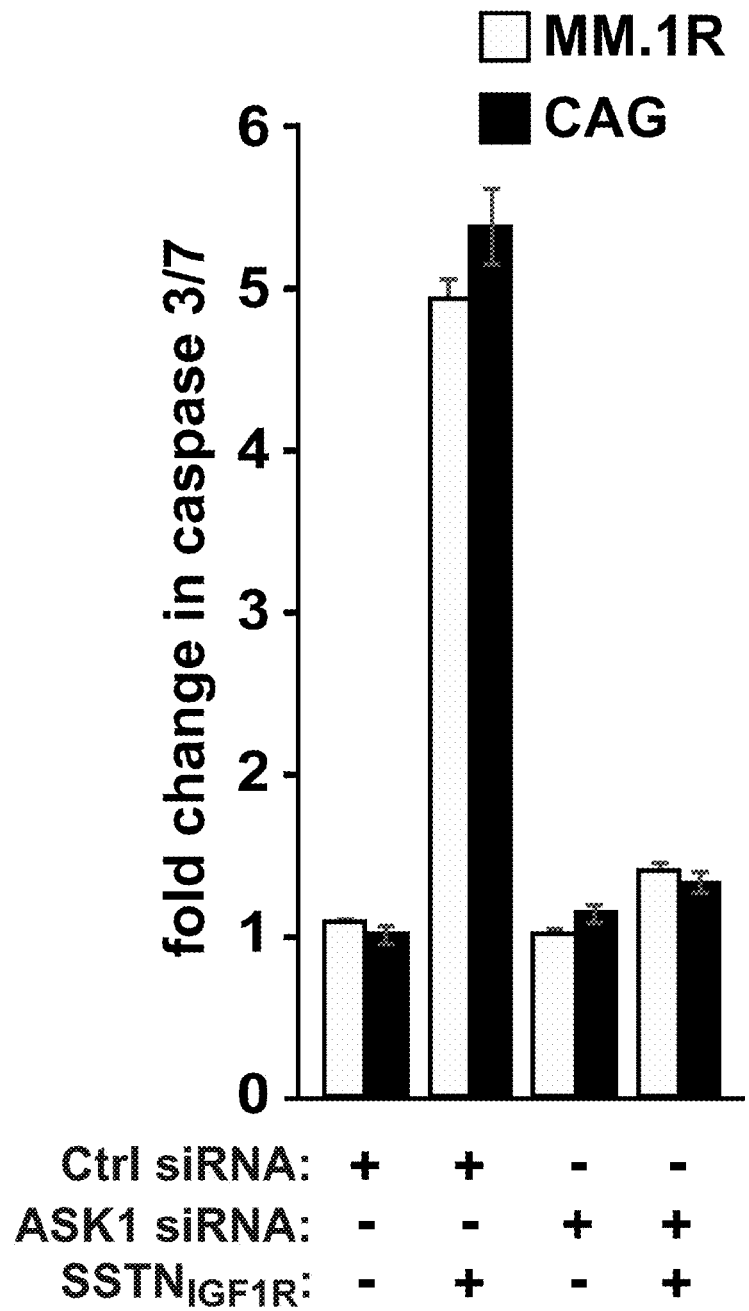
Figure 6C:
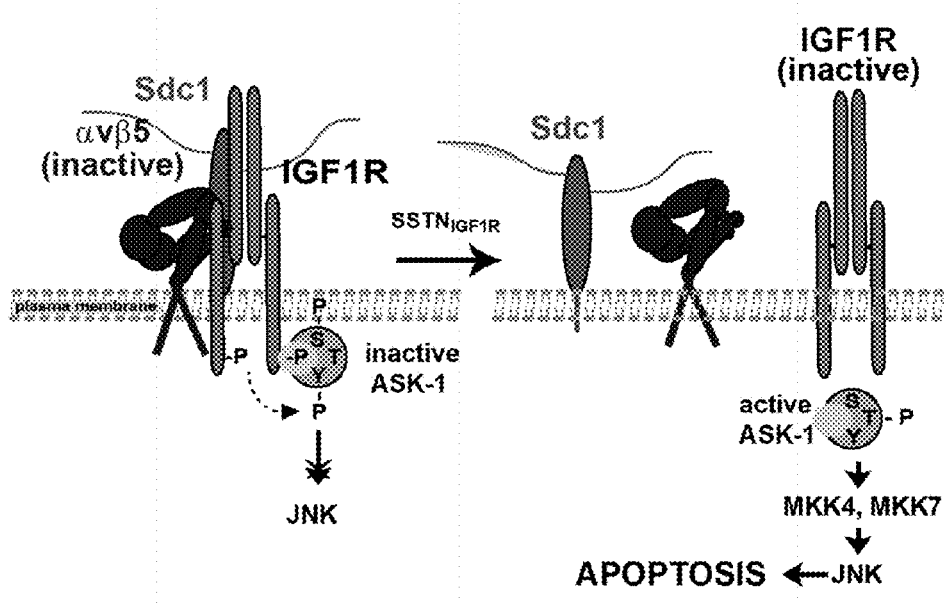
Figure 7:
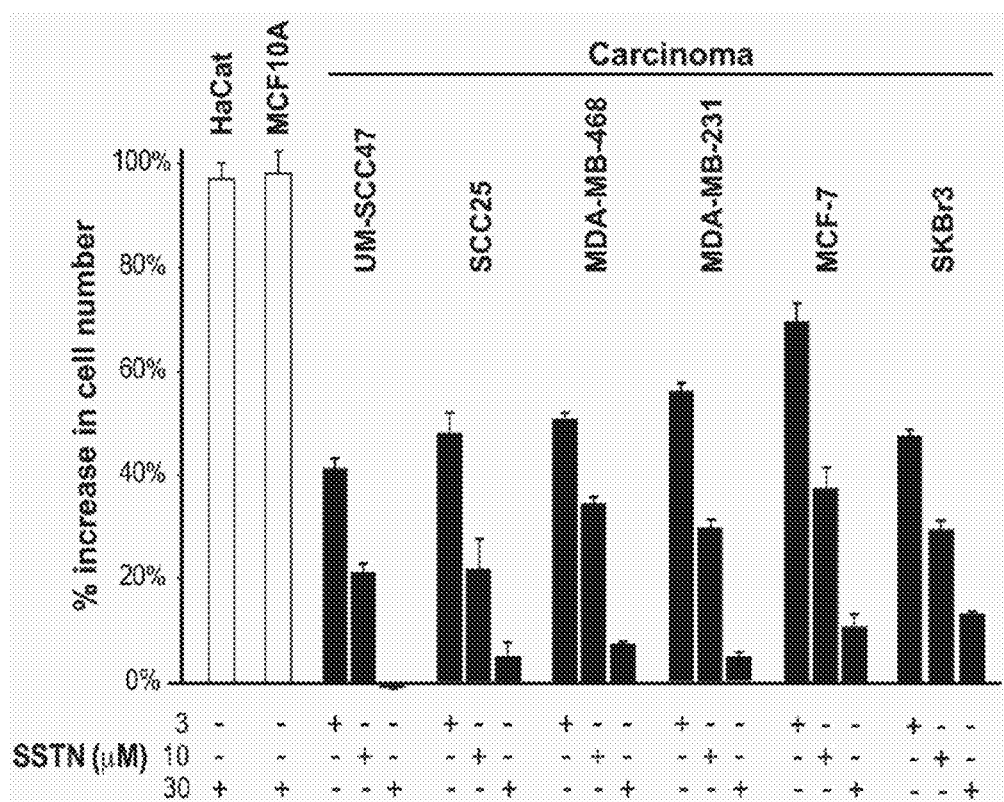
FIG. 7. $SSTN_{IGF1R}$ BLOCKS THE GROWTH OF BREAST AND HEAD & NECK CARCINOMA, BUT NOT NORMAL EPITHELIAL CELLS. Nontransformed HaCaT keratinocytes and MCF10A breast epithelial cells or UM-SCC47 and SCC25 Head & Neck squamous cell carcinoma, or MDA-MB-468, MDA-MB-231, MCF-7 and SKBr3 breast carcinoma cells are grown in 3, 10 or 30 µM $SSTN_{IGF1R}$ for 3 days. Cell growth/survival is graphed as % increase in cell number compared to untreated cells (Beauvais et al. 2016).

Perhaps the most effective role of $SSTN_{IGF1R}$ as a tumor therapeutic is its ability to kill tumor cells and activated endothelial cells. This is especially apparent in myeloma cells (FIGS. 4A and 4B). Tumor cells are under stress (DNA damage, metabolic stress, endoplasmic reticulum (ER) stress, stress from chemotherapeutic drugs, UV, IR, etc.), and stay alive and form tumors only if they have a mechanism to suppress this stress. Stress activates "apoptosis signal-regulating kinase-1," or ASK-1 (Dhanasekaran and Reddy 2008, Lin et al. 2012). It is a MAPKKK upstream of MKK4/MKK6 (MAPKKs) and the stress activated protein kinase/Jun N-terminal kinase (SAPK/JNK), a MAPK that activates apoptosis and causes cell death. Myeloma cells in particular are under stress, not only because of the stress that arises from them being a tumor cell, but also because they arise from immunoglobulin-secreting cells, and are secreting copious amounts of IgG themselves, which causes ER-stress. Thus, they remain alive only by inactivating ASK-1, and the Sdc1-coupled complex is one way in which they accomplish this. The inventors have shown that when Sdc1 captures IGF-1R and activates it, the active IGF-1R kinase captures and inactivates ASK-1 via tyrosine phosphorylation of the ASK-1 regulatory domain. By preventing IGF-1R activation by Sdc1, $SSTN_{IGF1R}$ prevents these events, SAPK/JNK becomes activated leading to apoptosis and cell death due to activation of executioner caspases (FIGS. 5, 6A, 6B and 6C). The inventors observe the induction of apoptosis by $SSTN_{IGF1R}$ in myeloma, vascular endothelial, breast carcinoma, cervical carcinoma and Head & Neck carcinoma, and anticipate this being the mechanism in many other tumors (FIG. 7). It is important to stress once again that normal and resting cells are not affected by the peptide (FIG. 7), because (a) they are not under stress, so ASK-1 is not activated and does not need to be suppressed by IGF-1R, and (b) they do not express the Sdc1-coupled IGF-1R complex.

II. $SSTN_{VLA4}$ AND $SSTN_{VEGFR2}$

Figure 8:
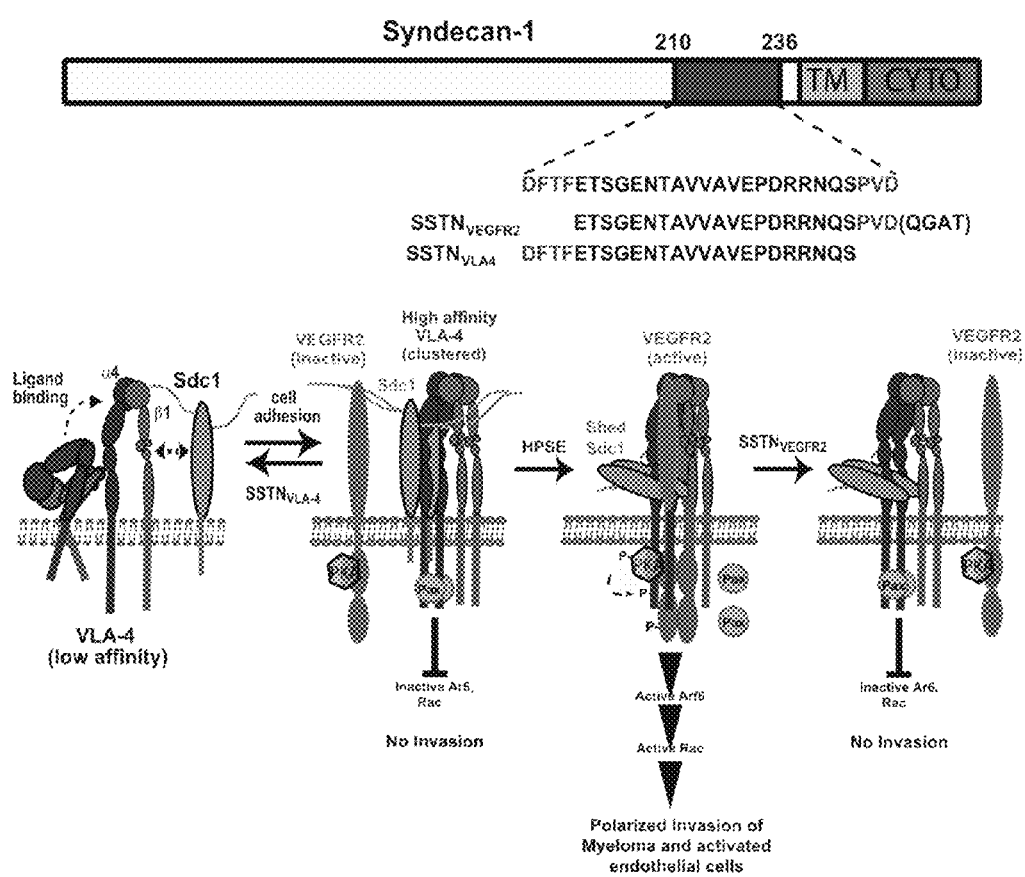
FIG. 8. MODEL OF SYNDECAN-1-MEDIATED ACTIVATION OF VLA-4 AND VEGFR2 AND INHIBITION BY $SSTN_{VLA4}$ OR $SSTN_{VEGFR2}$. A juxtamembrane region in the extracellular domain of Sdc1 (SEQ ID NO:12, aa210-236, top of three sequences in FIG. 8) contains overlapping docking sites for VLA-4 and VEGFR2. VLA-4 docking absolutely requires the DFTF motif (SEQ ID NO:13) at aa210-213, whereas VEGFR2 requires the PVD motif contained within aa214-236. A peptide that lacks the PVD motif (SEQ ID NO:14, $SSTN_{VLA4}$, aa210-233, bottom sequence in FIG. 8) competes for docking by VLA-4 but not VEGFR2, whereas a peptide that lacks the DFTF motif (SEQ ID NO:15, $SSTN_{VEGFR2}$, aa214-236 or 214-240, middle of three sequences in FIG. 8) prevents VEGFR2 capture. As shown in the model, the activation and clustering of VLA-4 to form high affinity adhesions with its ligands depends on its association with Sdc1, and $SSTN_{VLA4}$ blocks this adhesion. In addition, VLA-4-adherent cells are activated to polarize and invade if Sdc1 is shed, which allows the shed Sdc1 to engage both VLA-4 and VEGFR2, activating VEGFR2 by linking it to VLA-4 clusters. This does not require VEGF. VEGFR2 localized to the integrin activates protein kinase A (PKA), which phosphorylates that α4 integrin cytoplasmic domain, which displaces paxillin (Pax), a scaffolding protein that represses activation of Arf6 and its subsequent activation of Rac1. Releasing the suppression of Arf6 and Rac1 causes cytoskeletal rearrangement and extension of active lamellipodia necessary for invasion by myeloma cells and activated endothelial cells. This is prevented by $SSTN_{VEGFR2}$, which blocks VEGR2 capture and activation. $SSTN_{VLA4}$, however, blocks both processes. It prevents integrin activation by native, membrane intercalated Sdc1 and also blocks integrin-binding by shed Sdc1, thus preventing capture and activation of VEGFR2. (Modeled after (Jung et al. 2016)).
Figure 9A:
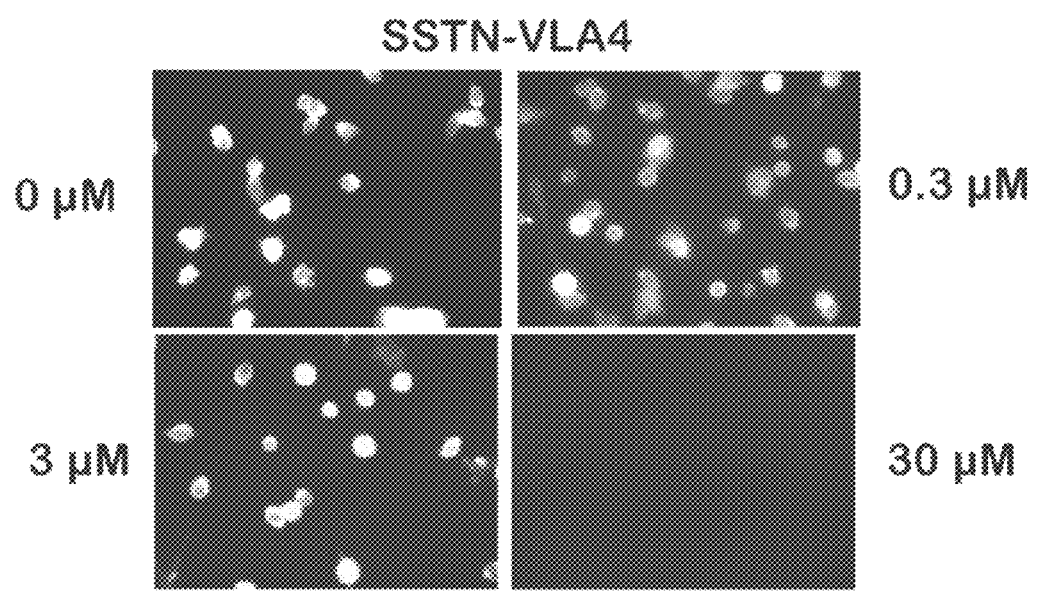
FIGS. 9A and 9B. $SSTN_{VLA4}$ BLOCKS VLA-4-MEDIATED ADHESION IN MYELOMA CELLS. 9A. Images of human CAG myeloma cells plated on FN for 2.5 hr to observe their VLA-4-mediated adhesion when treated with 0, 0.3, 3, or 30 µM of $SSTN_{VLA4}$, then fixed and stained with fluorescent phalloidin. 9B. Attached cells from five random images are quantified. (Modified from (Jung et al. 2016)).
Figure 9B:
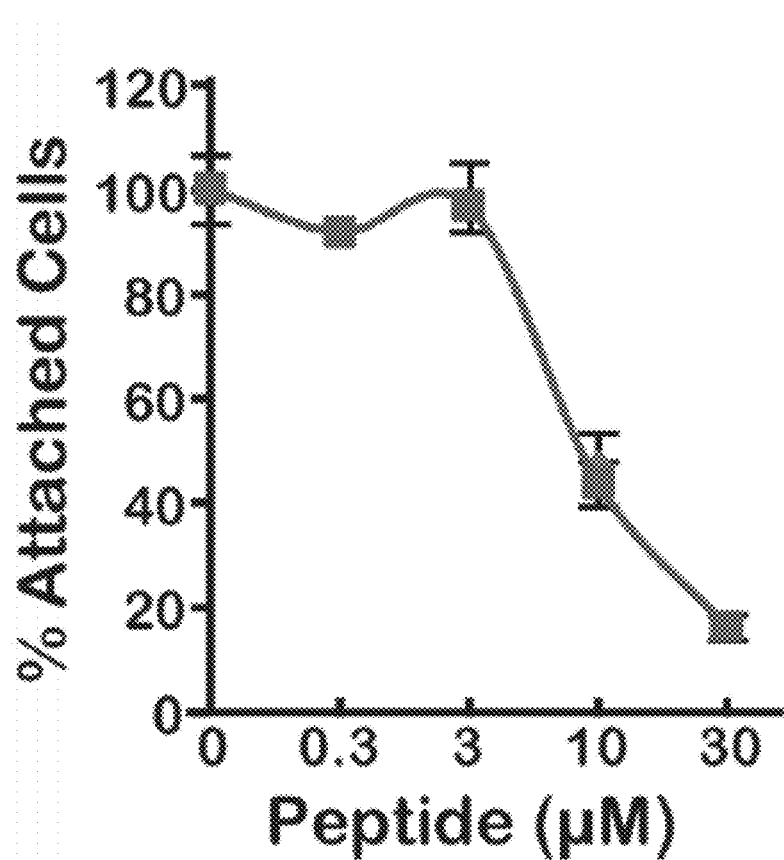

The inventors have now shown that Sdc1 is involved in the activation of VLA-4, the localization of VLA-4 to the leading edge of migrating myeloma and endothelial cells, and in the activation of PKA at this site. VLA-4 interacts directly with the Sdc1 extracellular domain, binding to a site with the juxtamembrane amino acids 210-233 of the syndecan (see model, FIG. 8). Amino acids 210-213 (asp-phe-thr-phe (DFTF, SEQ ID NO:13)) are especially important, as Sdc1 in which these amino acids have been deleted fails to bind VLA-4. When Sdc1 bearing this mutation ($\Delta$DFTF) is expressed, VLA-4 remains inactive and fails to promote adhesion of myeloma or vascular endothelial cells (Jung et al. 2016). Alternatively, in the presence of a peptide mimetic of the VLA-4 binding site ($SSTN_{VLA4}$ comprised of amino acids 210-233), adherent myeloma (FIGS. 9A and 9B) or endothelial cells (Jung et al, 2016) are displaced from VLA-4 ligands.

Figure 10A:
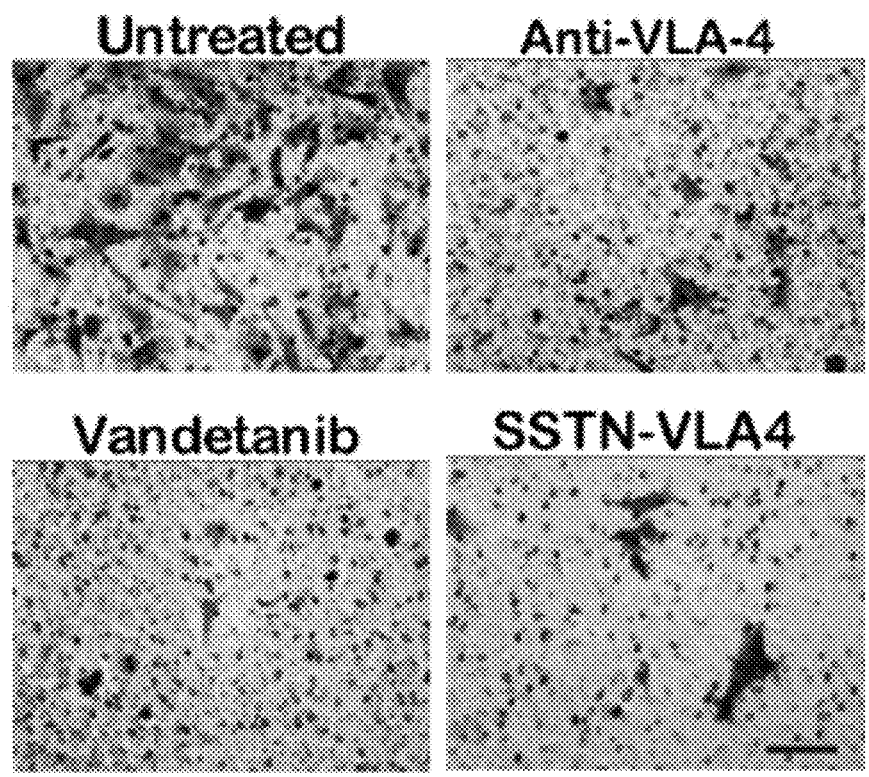
FIGS. 10A, 10B and 10C. $SSTN_{VLA4}$ BLOCKS ENDOTHELIAL CELL INVASION, VEGFR2 ACTIVATION AND TUBE FORMATION. 10A. 16 h transfilter migration assays towards the VLA-4 ligand GST-IIICS were performed using the human microvascular endothelial cell-1 cell line (HMEC-1) in the presence of VLA-4 blocking antibody, 30 µM $SSTN_{VLA4}$ or VEGFR2 inhibitor Vandetanib (Bar=100 µm); 10B. HMEC-1 cells were plated on IIICS for 2 h in the presence of 10 µM of $SSTN_{VLA4}$. Lysates were probed on immunoblots with antibodies against p1054/1059 of VEGFR2 to detect active receptor, or against total VEGFR2. Note that intervening lanes in the blot were removed for ease of comparison; 10C. HMEC-1 cells (2.5× $10^4$ cells/well) were seeded onto MATRIGEL® containing GST-IIICS and cultured in media containing 20 ng/ml VEGF in the absence or presence of 30 µM of $SSTN_{VLA4}$ for 24 h. Images of random fields were taken at 100× to observe capillary network formation (Bar=250 µm). (Modified from (Jung et al. 2016)).
Figure 10B:
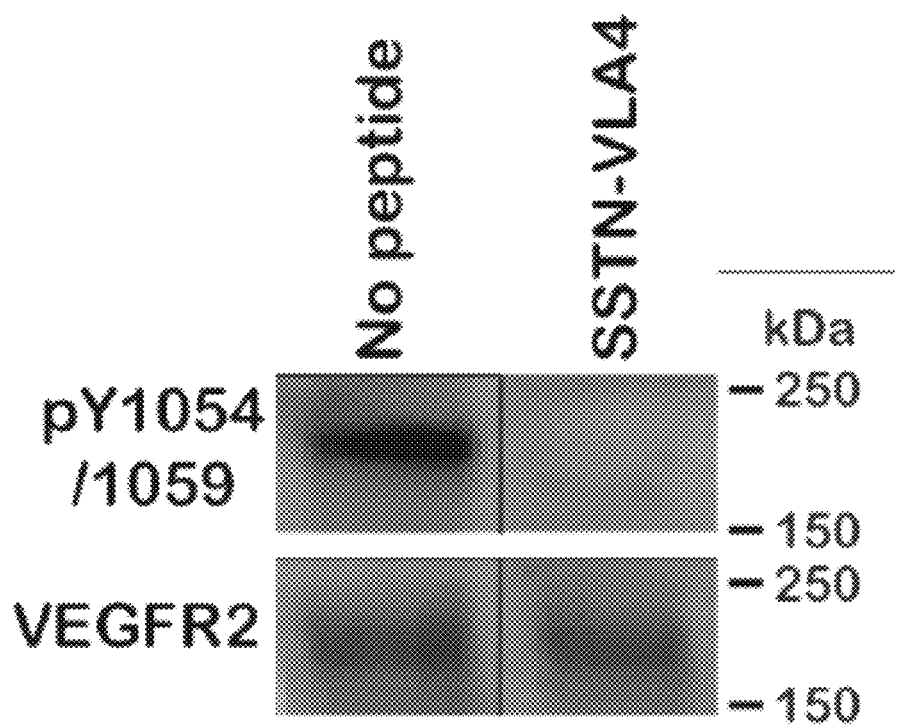
Figure 10C:
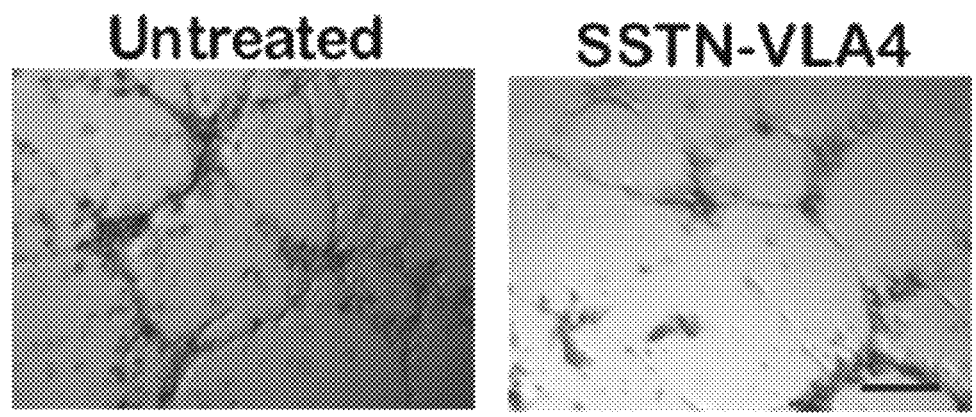

The inventors have also studied angiogenesis using in vitro assays (FIGS. 10A, 10B and 10C) and find that the same Sdc1-regulated mechanism exists on vascular endothelial cells. Endothelial cells utilize VLA-4 to bind to FN and VCAM-1 (note that FN is a common constituent of the stromal matrix in which angiogenesis occurs, and VCAM-1 is expressed on endothelial cells and encountered by VLA-4 during cell-cell contact). Polarized cell invasion (FIGS. 11A, 11B, 11C and 11D), and microvessel formation in an in vitro assay (FIGS. 10A, 10B and 10C) depends on VLA-4-mediated adhesion, and its activation of VEGFR2 (FIG. 10). This is prevented by $SSTN_{VLA4}$, which prevents VLA-4 docking to Sdc1 and thus prevents the angiogenic phenotype (FIGS. 10A, 10B and 10C).

Figure 11A:
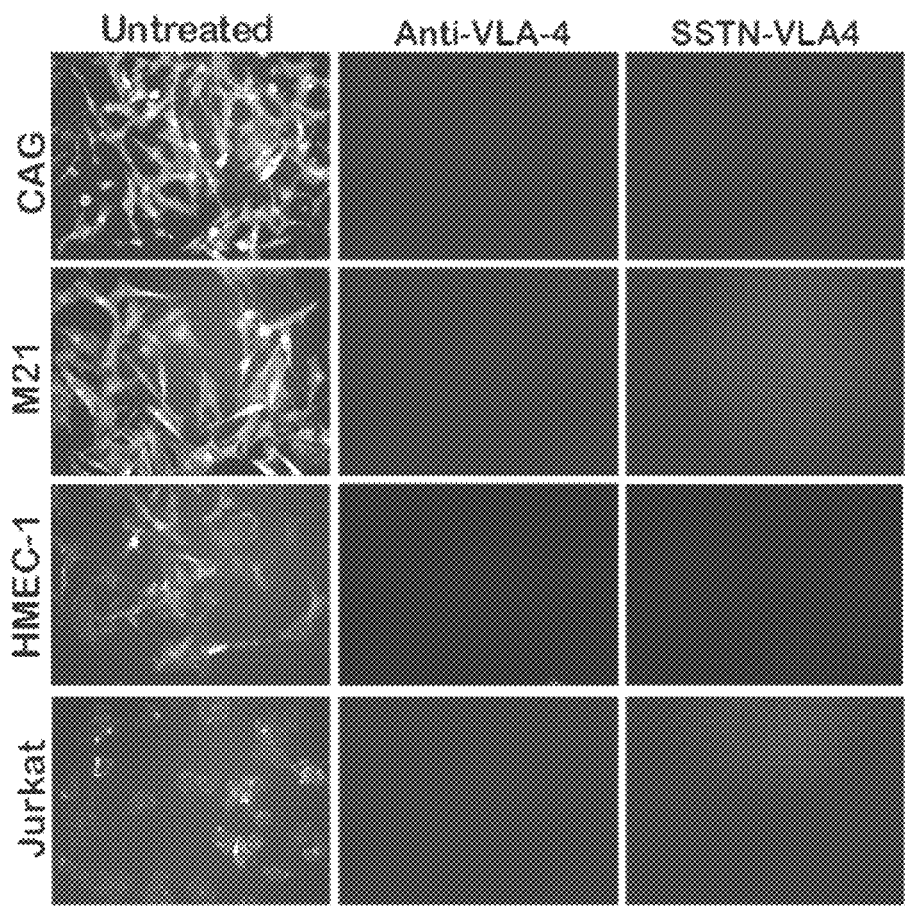
FIGS. 11A, 11B, 11C, and 11D. $SSTN_{VLA4}$ BLOCKS THE INVASION OF MYELOMA, MELANOMA, MICROVASCULAR ENDOTHELIAL AND T-LYMPHOMA CELLS ON VCAM-1. 11A. CAG myeloma, mouse M21 melanoma, human microvascular endothelial and Jurkat T-lymphoma cells are plated on VCAM-1 for 2 hr in the presence or absence of 30 µM $SSTN_{VLA4}$ or VLA-4 blocking antibody as a test of specificity. Numbers of adherent cells are quantified and expressed as a percentage of control, untreated cells in FIG. 11B. 11C. Cells are plated on top of filters coated with VCAM-1 allowed to migrate for 16 hr in the presence or absence of 30 µM $SSTN_{VLA4}$. Cells accumulating on the bottom of the filters are visualized by staining. 11D. Expression level of Sdc1 and VLA-4 are shown by Western blot staining of mouse natural killer (NK) and T-cells harvested from mouse spleens.
Figure 11B:
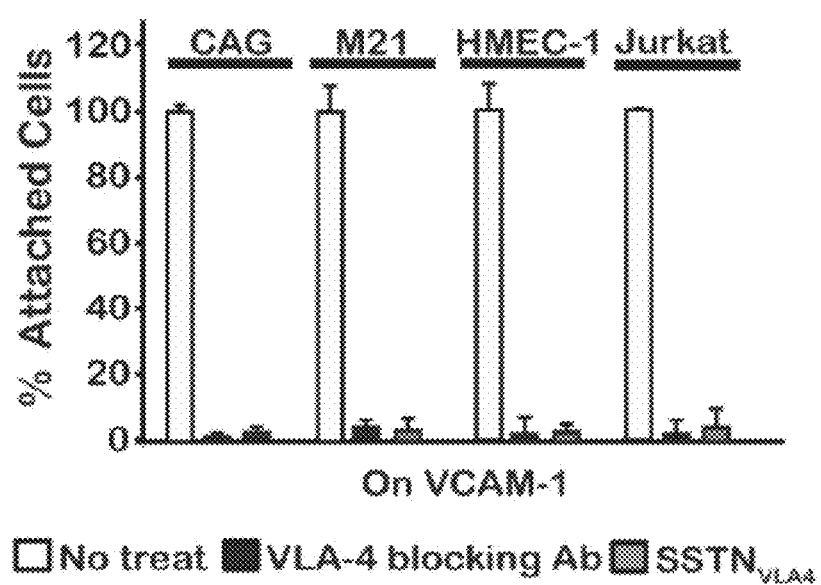
Figure 11C:
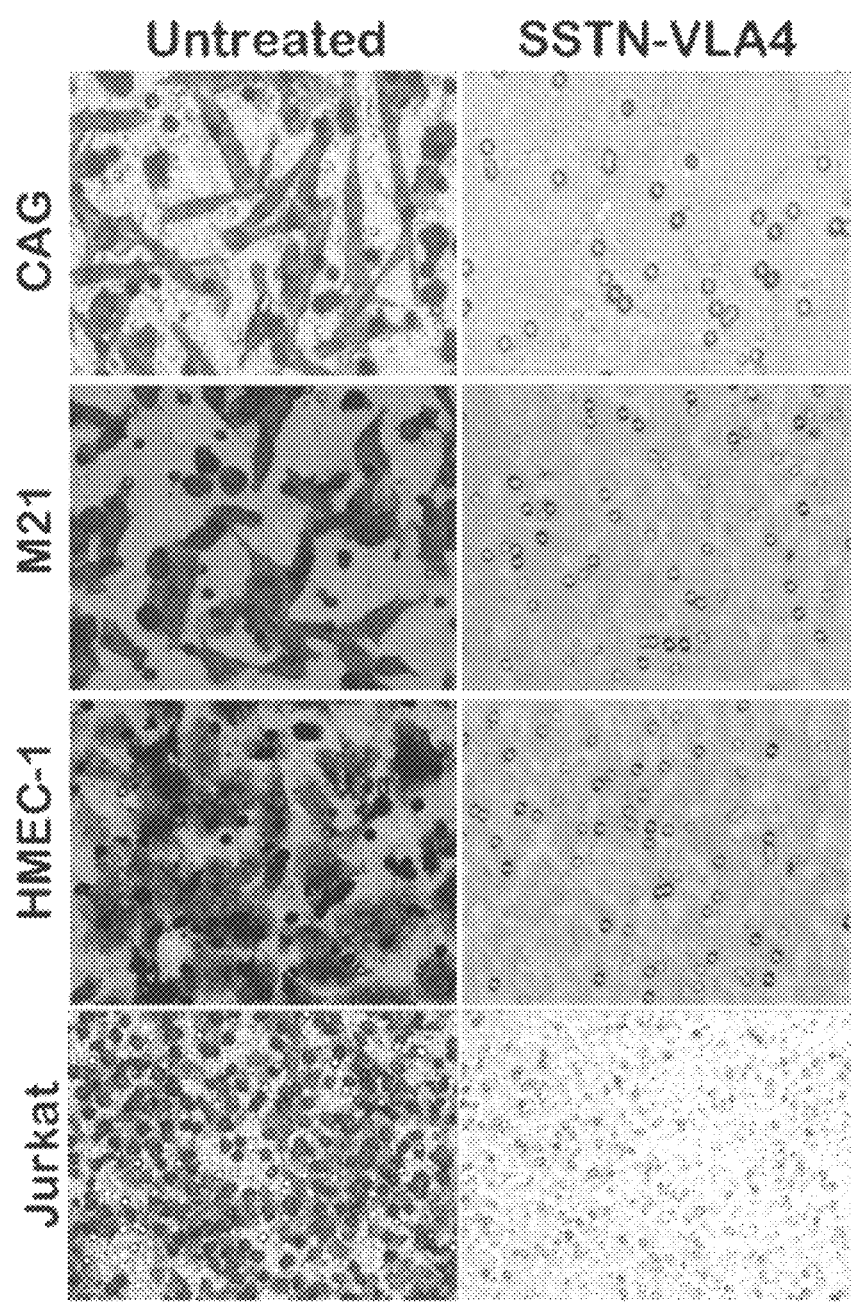
Figure 11D:
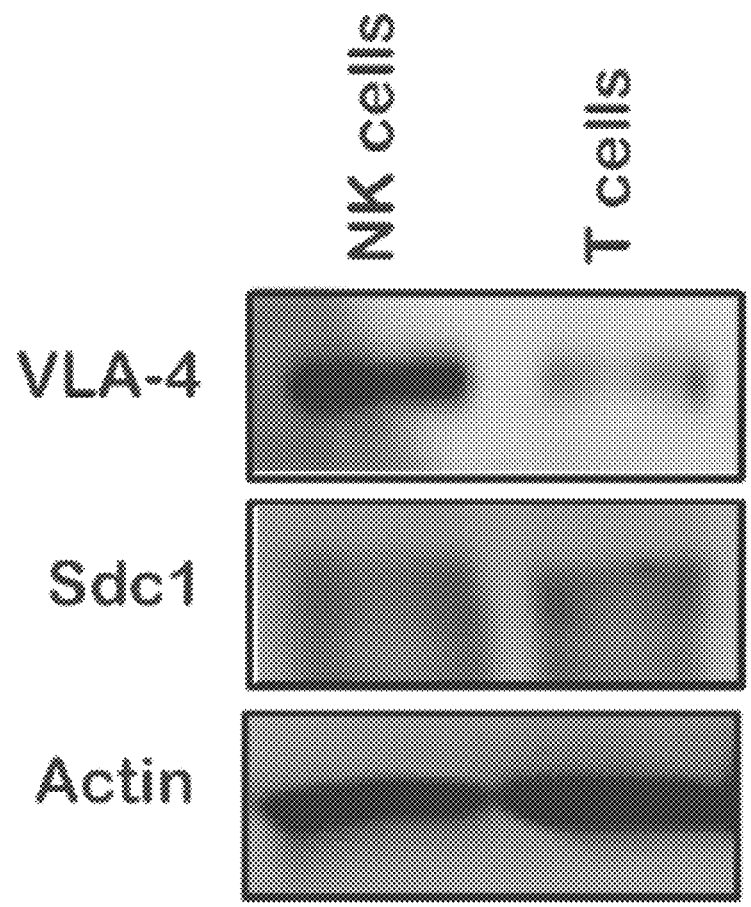

The inventors have discovered that the Sdc1-dependence of VLA-4 extends not only to myeloma and endothelial cells, but to other cells that express VLA-4 including melanoma and cells from the immune system where VLA-4 expression is common. The binding of myeloma, melanoma, microvascular endothelial and Jurkat T-lymphoma cells to the VLA-4 ligand VCAM-1 is prevented by $SSTN_{VLA-4}$ (FIG. 11A), as is the invasion of these cells through filters coated with this ligand (FIG. 11B). In addition, the inventors have shown that natural killer (NK) and T-cells, two immune cell types with roles in autoimmunity and tumor suppression, express both VLA-4 and its regulator Sdc1.

III. FUSION PEPTIDES

Syndecan-1 fusion peptides of the present disclosure will generally comprise molecules of 39 to about 100 residues in length, and will include SEQ ID NO:1 and SEQ ID NO:2, fused directly or via an inserted peptide or synthetic linker. A particular embodiment is SEQ ID NO:3. A particular length may be 39, 40, 41, 42, 43, 44, 45, 49, 50, 55, 60, 65, 70, 75, 80, 85, 90, 95, or 100 residues. Ranges of lengths include 39-50, 39-60, 39-70, 39-75, 39-80, 39-90 and 39-100 residues.

The peptides may be generated by recombinant techniques, and can be purified according to known methods, such as precipitation (e.g., ammonium sulfate), HPLC, ion exchange chromatography, affinity chromatography (including immunoaffinity chromatography) or various size separations (sedimentation, gel electrophoresis, gel filtration). Alternatively, the peptide maybe synthesized chemically, as discussed below.

Sequences that have between about 90% and 95%, or between about 90% and about 96%, or between about 90% and about 97%, or between about 90% and about 98% or or between about 90% and about 99% of amino acids that are identical or functionally equivalent to the amino acids of SEQ ID NOS:1, 2, or 3 are contemplated.

A. Substitutional Variants

As discussed above, it also is contemplated in the present disclosure that variants or analogs of syndecan-1 peptides may have the desired activities. Sequence variants of syndecan-1 peptides, primarily making conservative amino acid substitutions to SEQ ID NOS:1, 2, and 3 may even provide improved compositions. Substitutional variants typically contain the exchange of one amino acid for another at one or more sites within the protein, and may be designed to modulate one or more properties of the polypeptide, such as stability against proteolytic cleavage, without the loss of other functions or properties. Substitutions of this kind preferably are conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

The following is a discussion based upon changing of the amino acids of a peptide to create an equivalent, or even an improved, second-generation molecule. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a peptide that defines that peptide's biological functional activity, certain amino acid substitutions can be made in a protein sequence, and the underlying DNA coding sequence, and nevertheless obtain a peptide with like properties. It is thus contemplated by the inventors that various changes may be made in syndecan-1 amino acid sequences and in the DNA sequences coding the peptide without appreciable loss of their biological utility or activity, as discussed below.

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant peptide, which in turn defines the interaction of the peptide with other molecules.

Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a peptide with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine *−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent and immunologically equivalent protein. In such changes, the substitution of amino acids whose hydrophilicity values are within +2 is preferred, those that are within +1 are particularly preferred, and those within +0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take the various foregoing characteristics into consideration are well known to those of skill in the art and include: arginine and lysine; glutamate and aspartate; serine and threonine; glutamine and asparagine; and valine, leucine and isoleucine.

Another embodiment for the preparation of polypeptides according to the disclosure is the use of peptide mimetics. Mimetics are peptide containing molecules that mimic elements of protein secondary structure (Johnson et al, 1993). The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule. These principles may be used, in conjunction with the principles outline above, to engineer second generation molecules having many of the natural properties of syndecan-1, but with altered and even improved characteristics.

B. Altered Amino Acids

The present disclosure may employ peptides that comprise modified, non-natural and/or unusual amino acids. A table of exemplary, but not limiting, modified, non-natural and/or unusual amino acids is provided herein below. Chemical synthesis may be employed to incorporate such amino acids into the peptides of interest.

TABLE 1

Modified, Non-Natural and Unusual Amino Acids

| Abbr. | Amino Acid |
| --- | --- |
| Aad | 2-Aminoadipic acid |
| BAad | 3-Aminoadipic acid |
| BAla | beta-alanine, beta-Amino-propionic acid |
| Abu | 2-Aminobutyric acid |
| 4Abu | 4-Aminobutyric acid, piperidinic acid |
| Acp | 6-Aminocaproic acid |
| Ahe | 2-Aminoheptanoic acid |
| Aib | 2-Aminoisobutyric acid |
| BAib | 3-Aminoisobutyric acid |
| Apm | 2-Aminopimelic acid |
| Dbu | 2,4-Diaminobutyric acid |
| Des | Desmosine |
| Dpm | 2,2'-Diaminopimelic acid |
| Dpr | 2,3-Diaminopropionic acid |
| EtGly | N-Ethylglycine |
| EtAsn | N-Ethylasparagine |
| Hyl | Hydroxylysine |
| Ahyl | allo-Hydroxylysine |
| 3Hyp | 3-Hydroxyproline |
| 4Hyp | 4-Hydroxyproline |
| Ide | Isodesmosine |
| Aile | allo-Isoleucine |
| MeGly | N-Methylglycine, sarcosine |
| MeIle | N-Methylisoleucine |
| MeLys | 6-N-Methyllysine |
| MeVal | N-Methylvaline |
| Nva | Norvaline |
| Nle | Norleucine |
| Orn | Ornithine |

C. D Amino Acids

In another form, the present disclosure contemplates use of variants that comprise various portions of a syndecan-1 fusion peptide using "D amino acids," or stereoisomers of natural amino acids which are in the L-form.

D. Peptide Synthesis

Syndecan-1 fusion peptides may be generated synthetically for use in various embodiments of the present disclosure. Because of their relatively small size, the peptides of the disclosure can be synthesized in solution or on a solid support in accordance with conventional techniques. Various automatic synthesizers are commercially available and can be used in accordance with known protocols. See, for example, Stewart and Young (1984); Tam et al. (1983); Merrifield (1986); Barany and Merrifield (1979), each incorporated herein by reference. Alternatively, recombinant DNA technology may be employed wherein a nucleotide sequence which encodes a peptide of the disclosure is inserted into an expression vector, transformed or transfected into an appropriate host cell and cultivated under conditions suitable for expression (discussed elsewhere).

It may be desirable to purify syndecan-1 fusion peptide thereof. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography or even HPLC.

Certain aspects of the present disclosure concern the purification, and in particular embodiments, the substantial purification, of a peptide. The term "purified peptide" as used herein, is intended to refer to a composition, isolatable from other components, wherein the protein or peptide is purified to any degree relative to its naturally-obtainable state. A purified peptide therefore also refers to a peptide, free from the environment in which it may naturally occur.

Generally, "purified" will refer to a peptide composition that has been subjected to fractionation to remove various other components, and which composition substantially retains its expressed biological activity. Where the term "substantially purified" is used, this designation will refer to a composition in which the peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

Various techniques suitable for use in peptide purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the peptides always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a peptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size of the molecule. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography. The generation of antibodies that would be suitable for use in accord with the present disclosure is discussed below.

E. Linkers

Flexible linkers may be used to connect two or more peptide segments. These linkers may be rigid or flexible, the latter permitting more sterically independent function of the two joined segments. Flexible linkers, for example peptide linkers, generally are comprised of helix- and turn-promoting amino acid residues such as alanine, serine and glycine. However, other residues can function as well. Tang et al. (1996) used phage display as a means of rapidly selecting tailored linkers for single-chain antibodies (scFvs) from protein linker libraries.

Peptides can also be joined with a non-peptide linker or chemical unit. For example, cross-linking reagents can be used to form molecular bridges that tie functional groups of two different molecules, e.g., a stablizing and coagulating agent. To link two different compounds in a step-wise manner, hetero-bifunctional cross-linkers can be used that eliminate unwanted homopolymer formation.

An exemplary hetero-bifunctional cross-linker contains two reactive groups: one reacting with primary amine group (e.g., N-hydroxy succinimide) and the other reacting with a thiol group (e.g., pyridyl disulfide, maleimides, halogens, etc.). Through the primary amine reactive group, the cross-linker may react with the lysine residue(s) of one protein (e.g., the selected antibody or fragment) and through the thiol reactive group, the cross-linker, already tied up to the first protein, reacts with the cysteine residue (free sulfhydryl group) of the other protein (e.g., the selective agent).

It is preferred that a cross-linker having reasonable stability in blood will be employed. Numerous types of disulfide-bond containing linkers are known that can be successfully employed to conjugate targeting and therapeutic/preventative agents. Linkers that contain a disulfide bond that is sterically hindered may prove to give greater stability in vivo, preventing release of the targeting peptide prior to reaching the site of action. These linkers are thus one group of linking agents.

Another cross-linking reagent is SMPT, which is a bifunctional cross-linker containing a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to the delivery of the attached agent to the target site.

The SMPT cross-linking reagent, as with many other known cross-linking reagents, lends the ability to cross-link functional groups such as the SH of cysteine or primary amines (e.g., the epsilon amino group of lysine). Another possible type of cross-linker includes the hetero-bifunctional photoreactive phenylazides containing a cleavable disulfide bond such as sulfosuccinimidyl-2-(p-azido salicylamido) ethyl-1,3'-dithiopropionate. The N-hydroxy-succinimidyl group reacts with primary amino groups and the phenylazide (upon photolysis) reacts non-selectively with any amino acid residue.

In addition to hindered cross-linkers, non-hindered linkers also can be employed in accordance herewith. Other useful cross-linkers, not considered to contain or generate a protected disulfide, include SATA, SPDP and 2-iminothiolane (Wawrzynczak & Thorpe, 1987). The use of such cross-linkers is well understood in the art. Another embodiment involves the use of flexible linkers.

U.S. Pat. No. 4,680,338, describes bifunctional linkers useful for producing conjugates of ligands with amine-containing polymers and/or proteins, especially for forming antibody conjugates with chelators, drugs, enzymes, detectable labels and the like. U.S. Pat. Nos. 5,141,648 and 5,563,250 disclose cleavable conjugates containing a labile bond that is cleavable under a variety of mild conditions. This linker is particularly useful in that the agent of interest may be bonded directly to the linker, with cleavage resulting in release of the active agent. Particular uses include adding a free amino or free sulfhydryl group to a protein, such as an antibody, or a drug.

U.S. Pat. No. 5,856,456 provides peptide linkers for use in connecting polypeptide constituents to make fusion proteins, e.g., single chain antibodies. The linker is up to about 50 amino acids in length, contains at least one occurrence of a charged amino acid (preferably arginine or lysine) followed by a proline, and is characterized by greater stability and reduced aggregation. U.S. Pat. No. 5,880,270 discloses aminooxy-containing linkers useful in a variety of immunodiagnostic and separative techniques.

IV. NUCLEIC ACID SEGMENTS ENCODING SYNDECAN FUSION PEPTIDES

The present disclosure concerns nucleic acid segments, isolatable from cells, that are free from total genomic DNA and that are capable of expressing all or part of a syndecan-1 fusion peptide. As used herein, the term "nucleic acid segment" refers to a DNA molecule that has been isolated free of total genomic DNA of a particular species. Therefore, a nucleic acid segment encoding a syndecan-1 fusion peptide refers to a nucleic acid segment that contains wild-type, polymorphic, or mutant polypeptide-coding sequences yet is isolated away from, or purified free from, total mammalian or human genomic DNA. Included within the term "nucleic acid segment" are a polypeptide(s), nucleic acid segments smaller than a polypeptide, and recombinant vectors, including, for example, plasmids, cosmids, phage, viruses, and the like.

The term "cDNA" is intended to refer to DNA prepared using messenger RNA (mRNA) as template. The advantage of using a cDNA, as opposed to genomic DNA or DNA polymerized from a genomic, non- or partially-processed RNA template, is that the cDNA primarily contains coding sequences of the corresponding protein. There may be times when the full or partial genomic sequence is preferred, such as where the non-coding regions are required for optimal expression or where non-coding regions such as introns are to be targeted in an antisense strategy.

A nucleic acid segment encoding all or part of a fusion peptide may contain a contiguous nucleic acid sequence encoding all or a portion of such a polypeptide of the following lengths: 30, about 40, about 50, about 60, about 70, about 80, about 90, or about 100, about 110, about 120, about 130, about 140, about 150, about 160, about 170, about 180, about 190, about 200, about 210, about 220, about 230, about 240, about 250, about 260, about 270, about 280, about 290, or about 300 nucleotides, nucleosides, or base pairs. Specifically contemplated are a segment encoding SEQ ID NOs:1, 2 or 3.

The nucleic acid segments used in the present disclosure, regardless of the length of the coding sequence itself, may be combined with other nucleic acid sequences, such as promoters, enhancers polyadenylation signals, origin of replication, and a selectable marker gene, as well as other coding segments, and the like (all as are known to those of ordinary skill in the art), such that their overall length may vary considerably.

The term oligonucleotide refers to at least one molecule of between about 3 and about 100 nucleobases in length. These definitions generally refer to at least one single-stranded molecule, but in specific embodiments will also encompass at least one additional strand that is partially, substantially or fully complementary to the at least one single-stranded molecule. Thus, a nucleic acid may encompass at least one double-stranded molecule or at least one triple-stranded molecule that comprises one or more complementary strand(s) or "complement(s)" of a particular sequence comprising a strand of the molecule.

A nucleic acid sequence may encode additional heterologous coding sequences, for example to allow for linking of two peptides, purification of the peptide, transport, secretion, post-translational modification, or for therapeutic benefits such as targeting or efficacy.

In a non-limiting example, one or more nucleic acid constructs may be prepared that include a contiguous stretch of nucleotides identical to or complementary to a sequence encoding SEQ ID NOs:1, 2 or 3. Such a nucleic acid construct may be at least 20, 30, 40, 50, 60, 70, 80, 90, 100, 110, 120, 130, 140, 150, 160, 170, 180, 190, 200, 250, 300, 400, 500, 600, 700, 800, 900, 1,000, 2,000, 3,000, 4,000, 5,000, 6,000, 7,000, 8,000, 9,000, 10,000, 15,000, 20,000, 30,000, 50,000, 100,000, 250,000, 500,000, 750,000, to at least 1,000,000 nucleotides in length, as well as constructs of greater size, up to and including chromosomal sizes (including all intermediate lengths and intermediate ranges), given the advent of nucleic acids constructs such as a yeast artificial chromosome are known to those of ordinary skill in the art. It will be readily understood that "intermediate lengths" and "intermediate ranges," as used herein, means any length or range including or between the quoted values (i.e., all integers including and between such values).

In certain other embodiments, the disclosure concerns isolated nucleic acid segments and recombinant vectors that include within their sequence a contiguous nucleic acid sequence encoding SEQ ID NOs:1, 2 or 3. As recognized in the art, multiple different nucleic acid sequences may encode for the same amino acid sequence, and such nucleic acid sequences share the same or functionally equivalent codons. The term "functionally equivalent codon" is used herein to refer to codons that encode the same amino acid, such as the six codons for arginine or serine, and also refers to codons that encode biologically equivalent amino acids, as is known to those of skill in the art.

It also will be understood that this disclosure is not limited to one particular nucleic acid sequence. Recombinant vectors and isolated DNA segments may therefore variously include the syndecan-1-coding regions themselves, coding regions bearing selected alterations or modifications in the basic coding region, or they may encode larger polypeptides that nevertheless include syndecan-1-coding regions or may encode biologically functional equivalent proteins or peptides that have variant amino acids sequences.

The nucleic acid segments of the present disclosure encompass biologically functional equivalent syndecan-1 proteins and peptides. Such sequences may arise as a consequence of codon redundancy and functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the antigenicity of the protein.

If desired, one also may prepare fusion proteins and peptides, e.g., where the syndecan-1-coding regions are aligned within the same expression unit with other proteins or peptides having desired functions, such as for purification or immunodetection purposes (e.g., proteins that may be purified by affinity chromatography and enzyme label coding regions, respectively).

A. Promoters

The present disclosure may also involve expression of sdc-1 or related peptide from a sdc-1-encoding nucleic acid. This requires the presence of a promoter operably linked to the sdc-1-coding region. A promoter generally comprises a nucleic acid sequence that functions to position the start site for RNA synthesis. A promoter may or may not be used in conjunction with an enhancer, which refers to a cis-acting regulatory sequence involved in the transcriptional activation of a nucleic acid sequence. In the present disclosure, a nucleic acid encoding a sdc-1 comprises a promoter such as a tissue specific promoter, or a constitutive promoter, or an inducible promoter.

A promoter in the context of the present disclosure may be one naturally associated with a gene or sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter or enhancer, which refers to a promoter or enhancer that is not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. No. 4,683,202, U.S. Pat. No. 5,928,906, each incorporated herein by reference). Furthermore, it is contemplated the control sequences that direct transcription and/or expression of sequences within non-nuclear organelles such as mitochondria, chloroplasts, and the like, can be employed as well.

Those of skill in the art of molecular biology generally know the use of promoters, enhancers, and cell type combinations for protein expression, for example, see Sambrook et al. (2000), incorporated herein by reference.

The present disclosure also contemplates the use of tissue specific promoters and inducible promoters. Other promoters that may be employed with the present disclosure are constitutive and inducible promoters as are well known to those of skill in the art. Additionally any promoter/enhancer combination (as per the Eukaryotic Promoter Data Base EPDB) could also be used to drive expression of structural genes encoding oligosaccharide processing enzymes, protein folding accessory proteins, selectable marker proteins or a heterologous protein of interest.

B. Origins of Replication/Polyadenylation Signals

In expression, particularly eukaryotic expression, one will typically include a polyadenylation signal to effect proper polyadenylation of the transcript. The nature of the polyadenylation signal is not believed to be crucial to the successful practice of the disclosure. Polyadenylation signals include the SV40 polyadenylation signal and the bovine growth hormone polyadenylation signal, known to function well in various target cells. Polyadenylation may increase the stability of the transcript or may facilitate cytoplasmic transport.

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

C. Delivery of Nucleic Acids

Two broad approaches have been used to employ vectors to deliver nucleic acids to cells, namely viral vectors and non-viral vectors. As by methods described herein and as is known to the skilled artisan, expression vectors may be constructed to deliver nucleic acids segments encoding a syndecan-1 peptide of the present disclosure to a organelle, cell, tissue, or a subject. Such vectors comprising a syndecan-1 peptide may be used in a variety of manner consistent with the disclosure, including in screening assay and genetic immunization protocols.

A vector in the context of the present disclosure refers to a carrier nucleic acid molecule into which a nucleic acid sequence of the present disclosure may be inserted for introduction into a cell and thereby replicated. A nucleic acid sequence can be exogenous, which means that it is foreign to the cell into which the vector is being introduced; or that the sequence is homologous to a sequence in the cell but positioned within the host cell nucleic acid in which the sequence is ordinarily not found. Vectors include plasmids; cosmids; viruses such as bacteriophage, animal viruses, and plant viruses; and artificial chromosomes (e.g., YACs); and synthetic vectors. One of ordinary skill in the art would be well equipped to construct any number of vectors through standard recombinant techniques as described in Maniatis et al., 1990 and Ausubel et al., 1994, incorporated herein by reference.

Viral vectors may be derived from viruses known to those of skill in the art, for example, bacteriophage, animal and plant virus, including but not limited to, adenovirus, vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) retrovirus and herpesvirus and offer several features for use in gene transfer into various mammalian cells (Friedmann, 1989; Ridgeway, 1988; Baichwal and Sugden, 1986; Coupar et al., 1988; Horwich et al., 1990). One of skill in the art would be well equipped to construct a vector through standard recombinant techniques as described in Sambrook et al. (2001), Maniatis et al. (1990) and Ausubel et al. (1994), incorporated herein by reference. The present disclosure may also employ non-viral vectors.

An expression vector refers to any type of genetic construct comprising a nucleic acid coding for a RNA capable of being transcribed. In the context of the present specification, expression vectors will typically comprise a nucleic acid segment encoding a syndecan-1 peptide as described herein. In some cases, RNA molecules are then translated into a protein, polypeptide, or peptide. In other cases, these sequences are not translated, as in the case of antisense molecules or ribozymes production. Expression vectors can contain a variety of control sequences, which refer to nucleic acid sequences necessary for the transcription and possibly translation of an operably linked coding sequence in a particular host cell. In addition to control sequences that govern transcription and translation, vectors and expression vectors may contain nucleic acid sequences that serve other functions as well, and are described herein Non-viral vectors, such as plasmids and cosmids, require suitable method for delivery into cells. Such methods include, but are not limited to direct delivery of DNA by: injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), microinjection (Harland and Weintraub, 1985; U.S. Pat. No. 5,789,215, incorporated herein by reference); electroporation (U.S. Pat. No. 5,384,253, incorporated herein by reference; Tur-Kaspa et al., 1986; Potter et al., 1984); calcium phosphate precipitation (Graham and Van Der Eb, 1973; Chen and Okayama, 1987; Rippe et al., 1990); using DEAE-dextran followed by polyethylene glycol (Gopal, 1985); direct sonic loading (Fechheimer et al., 1987); by liposome-mediated transfection (Nicolau and Sene, 1982; Fraley et al., 1979; Nicolau et al., 1987; Wong et al., 1980; Kaneda et al., 1989; Kato et al., 1991); receptor-mediated transfection (Wu and Wu, 1987; Wu and Wu, 1988); microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); agitation with silicon carbide fibers (Kaeppler et al., 1990; U.S. Pat. Nos. 5,302,523 and 5,464,765, each incorporated herein by reference); desiccation/inhibition-mediated DNA uptake (Potrykus et al., 1985), and any combination of such methods. Through the application of techniques such as these, organelle(s), cell(s), tissue(s) or organism(s) may be stably or transiently transformed. In certain embodiments, acceleration methods are preferred and include, for example, microprojectile bombardment or inhalation methods.

Also in context of the present disclosure, topical delivery of a nucleic acid segment encoding a syndecan-1 peptide to the skin may further comprise vesicles such as liposomes, niosomes and transferosomes thereby enhancing topical and transdermal delivery. Cationic lipids may also be used to deliver negatively charged nucleic acids. Sonophoresis or phonophoresis which involves the use of ultrasound to deliver the nucleic acid of interest, may also be employed for transdermal delivery. Ionotophoresis which consists of applying a low electric field for a period of time to the skin may also be applied in delivering the nucleic acid of interest to the skin.

V. PHARMACEUTICAL FORMULATIONS, DELIVERY, AND CANCER TREATMENT REGIMENS

In particular embodiments of the present disclosure, a method of treatment for cancer by the delivery of a Sdc-1 fusion peptide as described elsewhere in this document is contemplated. Cancers contemplated by the present disclosure include, but are not limited to, breast cancer, lung cancer, head and neck cancer, bladder cancer, bone cancer, bone marrow cancer, brain cancer, colon cancer, esophageal cancer, gastrointestinal cancer, gum cancer, kidney cancer, liver cancer, nasopharynx cancer, ovarian cancer, prostate cancer, skin cancer, stomach cancer, testis cancer, tongue cancer, or uterine cancer. In particular embodiments, carcinomas, myelomas, melanomas or gliomas may be treated.

A. Administration

To treat cancer, one would generally contact a cell or tissue with a Sdc-1 fusion peptide or an expression construct encoding a Sdc-1 fusion peptide. The preferred method for the delivery of a fusion peptide or an expression construct is via injection. Administration may be parenteral, intradermal, intramuscular, or intratumoral administration. Other administration routes include lavage, continuous perfusion, topical and oral administration and formulation. See U.S. Pat. Nos. 5,543,158; 5,641,515; 5,399,363 (each specifically incorporated herein by reference in its entirety). Injection of nucleic acid constructs of the present disclosure may be delivered by syringe or any other method used for injection of a solution, as long as the expression construct can pass through the particular gauge of needle required for injection. A needleless injection system (U.S. Pat. No. 5,846,233); or a syringe system for use in gene therapy (U.S. Pat. No. 5,846,225), all as incorporated herein by reference, may be employed in the present disclosure.

B. Compositions and Formulations

Pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy syringability exists. Composition(s) of absorption delay agents (aluminum monostearate and gelatin) may also be used. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

For parenteral administration in an aqueous solution, for example, the solution should be suitably buffered if necessary and the liquid diluent first rendered isotonic with sufficient saline or glucose (see for example, "Remington's Pharmaceutical Sciences" 15th Edition, pages 1035-1038 and 1570-1580). These particular aqueous solutions are especially suitable for subcutaneous, intramuscular, and intratumoral administration. In this connection, sterile aqueous media that may be employed will be known to those of skill in the art in light of the present disclosure. Variation in dosage will necessarily occur depending on the condition of the subject being treated; the severity of the condition, and will be determined by the person administering the dose. For human administration, preparations should meet sterility, pyrogenicity, general safety and purity standards as required by FDA Office of Biologics standards.

The compositions of the present disclosure may be formulated in a neutral or salt form. Pharmaceutically-acceptable salts, include the acid addition salts (formed with the free amino groups of the protein) and which are formed with inorganic acids; or salts (formed with the free carboxyl groups) derived from inorganic bases as is known to those of ordinary skill in the art.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" or "pharmacologically-acceptable" refers to molecular entities and compositions that do not produce an allergic or similar untoward reaction when administered to a human. The preparation of an aqueous composition that contains a protein as an active ingredient is well understood in the art.

C. Combination Treatments

In the context of the present disclosure, it is contemplated that Sdc-1 fusion peptides thereof may be used in combination with an additional therapeutic agent to more effectively treat a cancer or other angiogenic diseases. Additional therapeutic agents contemplated for use in combination with Sdc-1 fusion peptides include, in the case of cancers, traditional anti-cancer therapies. Anticancer agents may include but are not limited to, radiotherapy, chemotherapy, gene therapy, hormonal therapy, surgery or immunotherapy that targets cancer/tumor cells.

To kill cells, induce cell-cycle arrest, inhibit migration, inhibit metastasis, inhibit survival, inhibit proliferation, or otherwise reverse or reduce the malignant phenotype of cancer cells, using the methods and compositions of the present disclosure, one would generally contact a cell with Sdc-1 fusion peptides in combination with an additional therapeutic agent. These compositions would be provided in a combined amount effective to inhibit cell growth and/or induce apoptosis in the cell.

For other angiogenic diseases, the combination therapy may include administration of a second anti-angiogenic therapy. This process may involve contacting the cells with Sdc-1 fusion peptide in combination with an additional therapeutic agent or factor(s) at the same time. This may be achieved by contacting the cell with a single composition or pharmacological formulation that includes both agents, or by contacting the cell with two distinct compositions or formulations, at the same time, wherein one composition includes the Sdc-1 peptides, proteins or derivatives thereof and the other includes the additional agent.

Alternatively, treatment with Sdc-1 fusion peptide may precede or follow the additional agent treatment by intervals ranging from minutes to weeks. In embodiments where the additional agent is applied separately to the cell, one would generally ensure that a significant period of time did not expire between the time of each delivery, such that the agent would still be able to exert an advantageously combined effect on the cell. In such instances, it is contemplated that one would contact the cell with both modalities within about 12-24 hr of each other and, more preferably, within about 6-12 hr of each other, with a delay time of only about 12 hr being most preferred. Thus, therapeutic levels of the drugs will be maintained. In some situations, it may be desirable to extend the time period for treatment significantly (for example, to reduce toxicity). Thus, several days (2, 3, 4, 5, 6 or 7) to several weeks (1, 2, 3, 4, 5, 6, 7 or 8) may lapse between the respective administrations.

It also is conceivable that more than one administration of either syndecan-1 peptides or analogs thereof in combination with an additional anticancer agent will be desired. Various combinations may be employed, where Sdc-1 fusion peptide is "A" and the additional therapeutic agent is "B", as exemplified below:

A/B/A B/A/B B/B/A A/A/B B/A/A A/B/B B/B/B/A B/B/A/B

A/A/B/B A/B/A/B A/B/B/A B/B/A/A B/A/B/A B/A/A/B B/B/B/A

A/A/A/B B/A/A/A A/B/A/A A/A/B/A A/B/B/B B/A/B/B B/B/A/B

Other combinations are contemplated. Some examples of combinations are set out below.

1. Chemotherapy

The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis. Most chemotherapeutic agents fall into the following categories: alkylating agents, antimetabolites, antitumor antibiotics, mitotic inhibitors, and nitrosoureas.

Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin γ1 and calicheamicin ω1; dynemicin, including dynemicin A uncialamycin and derivatives thereof; bisphosphonates, such as clodronate; an esperamicin; as well as neocarzinostatin chromophore and related chromoprotein enediyne anitbiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; antiadrenals such as aminoglutethimide, mitotane, trilostane; folic acid replenisher such as folinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel and docetaxel; chlorambucil; gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatraxate; daunomycin; aminopterin; xeloda; ibandronate; irinotecan (e.g., CPT-11); topoisomerase inhibitor RFS 2000; difluorometlhylomithine (DMFO); retinoids such as retinoic acid; capecitabine; cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, paclitaxel, docetaxel, gemcitabien, navelbine, farnesyl-protein tansferase inhibitors, transplatinum, 5-fluorouracil, vincristin, vinblastin and methotrexate and pharmaceutically acceptable salts, acids or derivatives of any of the above.

2. Radiotherapy

Radiotherapy, also called radiation therapy, is the treatment of cancer and other diseases with ionizing radiation. Ionizing radiation deposits energy that injures or destroys cells in the area being treated by damaging their genetic material, making it impossible for these cells to continue to grow. Although radiation damages both cancer cells and normal cells, the latter are able to repair themselves and function properly.

Radiation therapy used according to the present invention may include, but is not limited to, the use of γ-rays, X-rays, and/or the directed delivery of radioisotopes to tumor cells. Other forms of DNA damaging factors are also contemplated such as microwaves and UV-irradiation. It is most likely that all of these factors induce a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

Radiotherapy may comprise the use of radiolabeled antibodies to deliver doses of radiation directly to the cancer site (radioimmunotherapy). Antibodies are highly specific proteins that are made by the body in response to the presence of antigens (substances recognized as foreign by the immune system). Some tumor cells contain specific antigens that trigger the production of tumor-specific antibodies. Large quantities of these antibodies can be made in the laboratory and attached to radioactive substances (a process known as radiolabeling). Once injected into the body, the antibodies actively seek out the cancer cells, which are destroyed by the cell-killing (cytotoxic) action of the radiation. This approach can minimize the risk of radiation damage to healthy cells.

Conformal radiotherapy uses the same radiotherapy machine, a linear accelerator, as the normal radiotherapy treatment but metal blocks are placed in the path of the x-ray beam to alter its shape to match that of the cancer. This ensures that a higher radiation dose is given to the tumor. Healthy surrounding cells and nearby structures receive a lower dose of radiation, so the possibility of side effects is reduced. A device called a multi-leaf collimator has been developed and may be used as an alternative to the metal blocks. The multi-leaf collimator consists of a number of metal sheets which are fixed to the linear accelerator. Each layer can be adjusted so that the radiotherapy beams can be shaped to the treatment area without the need for metal blocks. Precise positioning of the radiotherapy machine is very important for conformal radiotherapy treatment and a special scanning machine may be used to check the position of internal organs at the beginning of each treatment.

High-resolution intensity modulated radiotherapy also uses a multi-leaf collimator. During this treatment the layers of the multi-leaf collimator are moved while the treatment is being given. This method is likely to achieve even more precise shaping of the treatment beams and allows the dose of radiotherapy to be constant over the whole treatment area.

Although research studies have shown that conformal radiotherapy and intensity modulated radiotherapy may reduce the side effects of radiotherapy treatment, it is possible that shaping the treatment area so precisely could stop microscopic cancer cells just outside the treatment area being destroyed. This means that the risk of the cancer coming back in the future may be higher with these specialized radiotherapy techniques.

Scientists also are looking for ways to increase the effectiveness of radiation therapy. Two types of investigational drugs are being studied for their effect on cells undergoing radiation. Radiosensitizers make the tumor cells more likely to be damaged, and radioprotectors protect normal tissues from the effects of radiation. Hyperthermia, the use of heat, is also being studied for its effectiveness in sensitizing tissue to radiation.

3. Immunotherapy

In the context of cancer treatment, immunotherapeutics, generally, rely on the use of immune effector cells and molecules to target and destroy cancer cells. Trastuzumab (Herceptin™) is such an example. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells. The combination of therapeutic modalities, i.e., direct cytotoxic activity and inhibition or reduction of ErbB2 would provide therapeutic benefit in the treatment of ErbB2 overexpressing cancers.

In one aspect of immunotherapy, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155. An alternative aspect of immunotherapy is to combine anticancer effects with immune stimulatory effects. Immune stimulating molecules also exist including: cytokines such as IL-2, IL-4, IL-12, GM-CSF, γ-IFN, chemokines such as MIP-1, MCP-1, IL-8 and growth factors such as FLT3 ligand. Combining immune stimulating molecules, either as proteins or using gene delivery in combination with a tumor suppressor has been shown to enhance anti-tumor effects (Ju et al., 2000). Moreover, antibodies against any of these compounds may be used to target the anti-cancer agents discussed herein.

Examples of immunotherapies currently under investigation or in use are immune adjuvants e.g., *Mycobacterium bovis, Plasmodium falciparum*, dinitrochlorobenzene and aromatic compounds (U.S. Pat. Nos. 5,801,005 and 5,739, 169; Hui and Hashimoto, 1998; Christodoulides et al., 1998), cytokine therapy, e.g., interferons α, β, and γ; IL-1, GM-CSF and TNF (Bukowski et al., 1998; Davidson et al., 1998; Hellstrand et al., 1998) gene therapy, e.g., TNF, IL-1, IL-2, p53 (Qin et al., 1998; Austin-Ward and Villaseca, 1998; U.S. Pat. Nos. 5,830,880 and 5,846,945) and monoclonal antibodies, e.g., anti-ganglioside GM2, anti-HER-2, anti-p185 (Pietras et al., 1998; Hanibuchi et al., 1998; U.S. Pat. No. 5,824,311). It is contemplated that one or more anti-cancer therapies may be employed with the gene silencing therapies described herein.

In active immunotherapy, an antigenic peptide, polypeptide or protein, or an autologous or allogenic tumor cell composition or "vaccine" is administered, generally with a distinct bacterial adjuvant (Ravindranath and Morton, 1991; Morton et al., 1992; Mitchell et al., 1990; Mitchell et al., 1993).

In adoptive immunotherapy, the patient's circulating lymphocytes, or tumor infiltrated lymphocytes, are isolated in vitro, activated by lymphokines such as IL-2 or transduced with genes for tumor necrosis, and readministered (Rosenberg et al., 1988; 1989).

4. Surgery

Approximately 60% of persons with cancer will undergo surgery of some type, which includes preventative, diagnostic or staging, curative, and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present invention may be used in conjunction with removal of superficial cancers, precancers, or incidental amounts of normal tissue.

Upon excision of part or all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

In some particular embodiments, after removal of the tumor, an adjuvant treatment with a compound of the present disclosure is believe to be particularly efficacious in reducing the reoccurance of the tumor. Additionally, the compounds of the present disclosure can also be used in a neoadjuvant setting.

5. Other Agents

It is contemplated that other agents may be used with the present invention. These additional agents include immunomodulatory agents, agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Immunomodulatory agents include tumor necrosis factor; interferon alpha, beta, and gamma; IL-2 and other cytokines; F42K and other cytokine analogs; or MIP-1, MIP-1β, MCP-1, RANTES, and other chemokines. It is further contemplated that the upregulation of cell surface receptors or their ligands such as Fas/Fas ligand, DR4 or DR5/TRAIL (Apo-2 ligand) would potentiate the apoptotic inducing abilities of the present invention by establishment of an autocrine or paracrine effect on hyperproliferative cells. Increasing intercellular signaling by elevating the number of GAP junctions would increase the anti-hyperproliferative effects on the neighboring hyperproliferative cell population. In other embodiments, cytostatic or differentiation agents may be used in combination with the present invention to improve the anti-hyerproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present invention to improve the treatment efficacy.

There have been many advances in the therapy of cancer following the introduction of cytotoxic chemotherapeutic drugs. However, one of the consequences of chemotherapy is the development/acquisition of drug-resistant phenotypes and the development of multiple drug resistance. The development of drug resistance remains a major obstacle in the treatment of such tumors and therefore, there is an obvious need for alternative approaches such as gene therapy.

Another form of therapy for use in conjunction with chemotherapy, radiation therapy or biological therapy includes hyperthermia, which is a procedure in which a patient's tissue is exposed to high temperatures (up to 106° F.). External or internal heating devices may be involved in the application of local, regional, or whole-body hyperthermia. Local hyperthermia involves the application of heat to a small area, such as a tumor. Heat may be generated externally with high-frequency waves targeting a tumor from a device outside the body. Internal heat may involve a sterile probe, including thin, heated wires or hollow tubes filled with warm water, implanted microwave antennae, or radiofrequency electrodes.

A patient's organ or a limb is heated for regional therapy, which is accomplished using devices that produce high energy, such as magnets. Alternatively, some of the patient's blood may be removed and heated before being perfused into an area that will be internally heated. Whole-body heating may also be implemented in cases where cancer has spread throughout the body. Warm-water blankets, hot wax, inductive coils, and thermal chambers may be used for this purpose.

The skilled artisan is directed to "Remington's Pharmaceutical Sciences" 15th Edition, chapter 33, in particular pages 624-652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards. It also should be pointed out that any of the foregoing therapies may prove useful by themselves in treating cancer.

VI. TREATING AUTOIMMUNE DISEASE

The present disclosure also contemplates the use of syndecan-1 fusion peptides to inhibit immune function in the context of autoimmune diseases. Autoimmune diseases include rheumatoid arthritis, psoratic arthritis, systemict lupus erythematosus, celiac disese, Sjögren's syndrome, polymyalgia rheumatica, multiple sclerosis, ankylosing spondylitis, Type 1 diabetes, Crohn's disease, uclerative colitis, alopecia areata, vasculitis and temporal arteritis, among others.

In general, administration of autoimmune therapeutics is through a systemic approach, such as intravenous or oral administration. However, it may be desirable to target administration to a particular site, such as topical, intra-articular or enteric release administrations. In addition, combination therapies are available for some autoimmune diseases and include steroids and other anti-inflammatories, as well as anti-rheumatic drugs.

VII. EXAMPLES

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—Materials and Methods

Reagents.

SSTN peptides obtained from LifeTEIN LLC (Hillsborough, N.J.) were reconstituted as a concentrated stock at 600 μM in DMEM (Life Technologies, Grand Island, N.Y.) containing 200 mM HEPES (Sigma-Aldrich, St. Louis, Mo.) and 0.1% heat-denatured BSA, then diluted as needed for cell adhesion or cell viability studies. GRGDSP peptide (SEQ ID NO:31) was obtained from EMD Millipore and reconstituted in DMEM and HEPES as described for the SSTNs. CellTiter-GLO was from Promega Corp. (Madison, Wis.).

Cell Viability Assays.

All cells were cultured at 37° C. and 92.5% air/7.5% $CO_2$. The derivation and culture of CAG myeloma and HMEC-1 cells are described previously (Ades et al. 1992, Rapraeger et al. 2013). B78 murine melanoma cells were kindly provided by Dr. Sondel, Department of Pediatrics, University of Wisconsin-Madison. All cells are routinely screened for mycoplasma contamination. For viability studies, $2.5 \times 10^4$ myeloma cells/well or $10^4$ B78 murine melanoma cells were plated in 96-well plates in complete DMEM containing 10% calf serum in the presence or absence of SSTN peptides for 24, 48 or 72 hrs. Numbers of viable cells were then determined by addition of CellTiter-GLO reagent to the culture medium as described by the manufacturer and viable cells determined by staining with 0.4% trypan blue and counting cells that exclude (viable) or take up (dead) the stain.

Cell Adhesion and Spreading Assays.

Nitrocellulose-treated slides (Lebakken and Rapraeger 1996) were coated for 2 h at 37° C. with 100 μg/ml recombinant GST-IIICS fragment (Lebakken et al. 2000) in calcium and magnesium-free PBS (CMF-PBS; 135 mM NaCl, 2.7 mM KCl, 10.2 mM $Na_2HPO_4$-$7H_2O$ and 1.75 mM $KH_2PO_4$, pH7.4), then blocked with RPMI-1640 containing 1% heat-denatured BSA (plating medium). $2.5 \times 10^4$ CAG myeloma, $1.0 \times 10^4$ HMEC-1 or $10^3$ B78 murine melanoma cells in plating medium were allowed to attach and spread for 2.5 h at 37° C., fixed in 4% paraformaldehyde (Electron Microscopy Sciences) in CMF-PBS, labeled with rhodamine phalloidin (Invitrogen) and imaged with a Nikon Microphot FX microscope using a 20× objective (Nikon; Ex 541-551, DM 580, Barrier 590), Photometric CoolSnap ES camera, and version 7.7.3.0 Metamorph© Imaging software (Molecular Devices). Adherent cells were quantified by counting cells in triplicate wells.

SSTN Stability Assay

For stability assays, $SSTN_{IGF1R}$, $SSTN_{VLA4}$, $SSTN_{I/V}$ and GRGDSP peptide (SEQ ID NO:31; EMD Millipore) were incubated in human plasma (obtained from the UW-Madison Hospital Blood Bank) for 0, 8, 24 or 72 hr, then tested in the endothelial cell adhesion assay or cell viability assay and compared to a standard curve generated using fresh peptide.

Example 2—Results

The inventors' prior published work has shown that the matrix receptor syndecan-1 (Sdc1/CD138), a matrix receptor highly expressed in multiple myeloma, captures and activates multiple cell surface receptors, among them the insulin-like growth factor-1 receptor (IGF-1R) and very late antigen-4 (VLA-4, also known as the α4β1 integrin). The inventors have shown that IGF-1R provides survival signaling for many tumor cells, including myeloma, as well as for activated endothelial cells. VLA-4 is expressed on leukocytes (lymphoid and myeloid) and their malignant counterparts, including myeloma, and has a major role in cell adhesion, extravasation from the blood stream and invasion. VLA-4 provides resistance to chemotherapy, a mechanism known as Cell Adhesion-Mediated Drug Resistance or CAM-DR. The inventors have shown that Sdc1-mediated activation of VLA-4 is critical for adhesion and enhanced invasion of myeloma cells and activated endothelial cells undergoing angiogenesis, an important contributor to tumor growth. Thus, targeting one or both of these important receptors with a single drug holds great promise for disrupting cancer growth.

Figures 13A, 13B:
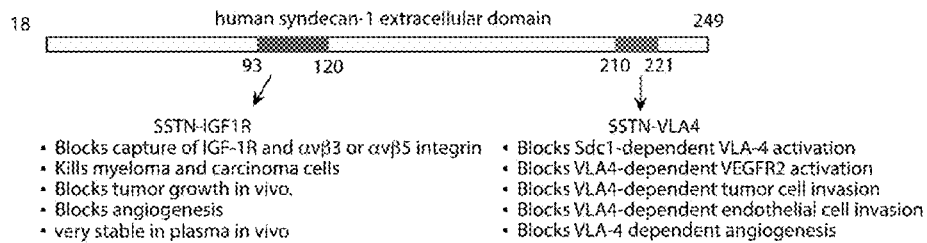
Figure 14:
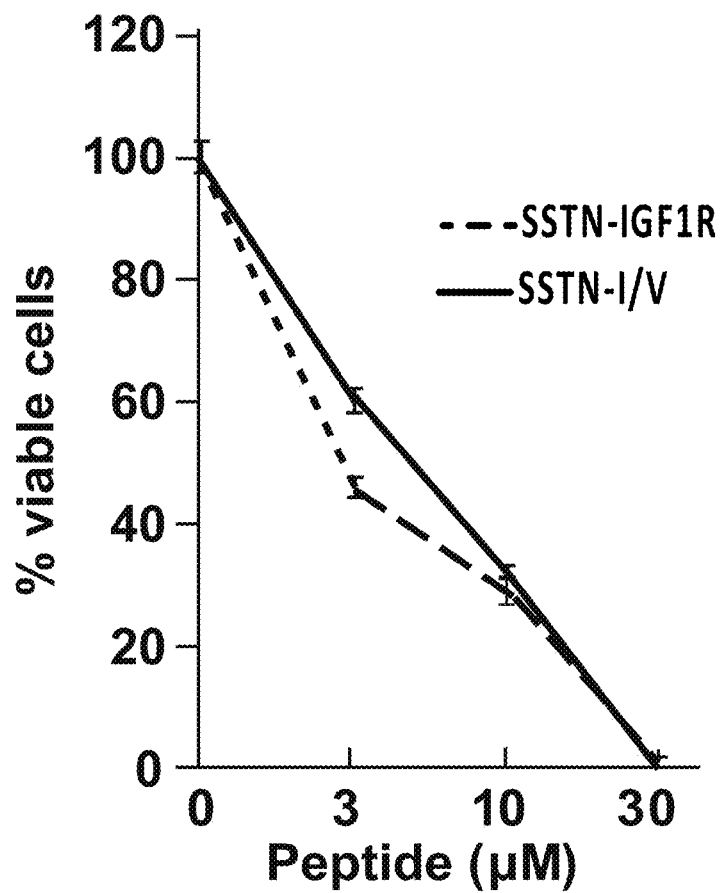
FIG. 14. $SSTN_{I/V}$ KILLS MYELOMA CELLS EQUIVALENT TO $SSTN_{IGF1R}$. CAG myeloma cells were cultured for 3 days in the presence or absence of up to 30 µM $SSTN_{IGF1R}$ or $SSTN_{I/V}$. Cell lysates were subjected to analysis using CellTiter-GLO and the percentage of viable cells plotted as a percentage of untreated cells.

The capture of these two receptors by human Sdc1 is mediated by two distinct sites in the extracellular domain of the syndecan (FIG. 13A). Amino acids 93-120 comprise the minimal site that will capture IGF-1R (FIGS. 2, 3). The juxtamembrane site in human Sdc1 comprised of amino acids 210-233 contains the VLA-4 interaction site and the inventors have now shown that a peptide comprised of amino acids 210-221 suffices for full inhibitory activity (FIG. 12), with the DFTF motif at the N-terminus of the peptide being essential to bind VLA-4 (Jung et al., 2016). The inventors reasoned that a single, novel combination peptide containing both activities would allow more effective treatment of tumors or immune diseases than either peptide alone. However, since removal of even one amino acid from the C-terminus of $SSTN_{IGF1R}$ dramatically reduces its activity (FIG. 3), and the DFTF motif (SEQ ID NO: 13) at the N-terminus of the $SSTN_{VLA4}$ is equally critical for VLA-4 binding and the inhibitory activity of the $SSTN_{VLA4}$ peptide (FIG. 12), the inventors were concerned that simply fusing two unrelated protein sequences together would prevent the inhibitory activity of one or both of the parent peptides, as the critical amino acids present at the terminus of either of the free peptides may find themselves enmeshed in an amino acid protein sequence that could easily alter their active conformation.

This concern was alleviated to some degree when the inventors noticed a conserved charged motif (glutamate-glutamine-glutamate or EQE) at the C-terminus of $SSTN_{IGF1R}$ as well as a highly homologous EQD (glutamate-glutamine-aspartate) motif in the sequence of Sdc1 just upstream and including the N-terminus of $SSTN_{VLA4}$ (FIG. 13B). Based on this discovery, the inventors reasoned that both inhibitory activities might be sustained in a single fusion protein if $SSTN_{IGF1R}$ were fused to the N-terminus of $SSTN_{VLA4}$, substituting EQD for EQE in $SSTN_{IGF1R}$, and ensuring that the N-terminus of $SSTN_{VLA4}$ is just downstream of this charged motif as it is in the native Sdc1 protein (FIG. 13C). In this manner, the amino acids derived from $SSTN_{IGF1R}$ and those from $SSTN_{VLA4}$ would find themselves in a native conformational environment despite being joined together. This new peptide is called "Synstatin-IGF-1R/VLA-4" or "$SSTN_{I/V}$". Other peptides analyzed included fusing both Sdc1 domains together, interspersed with a polyalanine motif (AAAA; SEQ ID NO:4) to allow for flexibility, fusing the minimal peptides together with the polyalanine motif, or using direct fusion via the conserved charged motif (FIG. 13D). As documented in the following figures (FIGS. 14-18), this $SSTN_{I/V}$ peptide blocks VLA-4-mediated adhesion of myeloma cells and activated endothelial cells, induces apoptosis in myeloma cells by inhibiting IGF-1R and blocks invasion of melanoma cells that depends on both avb3 integrin (blocked by $SSTN_{IGF1R}$) and VLA-4 (blocked by $SSTN_{VLA4}$). Importantly, it is also highly stable in serum, in which most peptides are rapidly destroyed by exoproteases. It is envisioned to block cell survival and invasion of numerous cancer cells, to block tumor-induced angiogenesis and to regulate homing of lymphoid and myeloid leukocytes in immune diseases, lymphomas/leukemias and to either prevent the support (myeloid cells) or enhance the killing (T-cells) of solid tumors and blood cancers. These and other aspects of the disclosure are set out in the discussion below.

Figure 15:
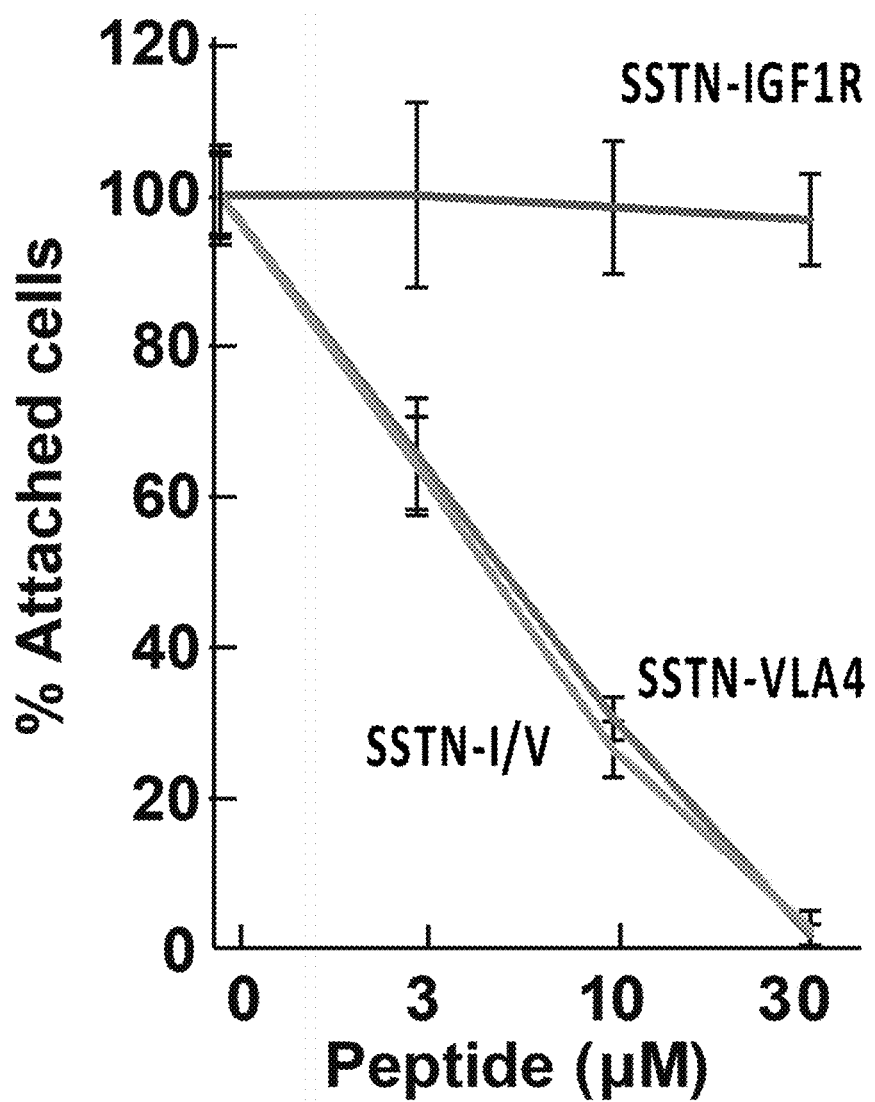
FIG. 15. $SSTN_{I/V}$ BLOCKS VLA-4-MEDIATED ENDOTHELIAL CELL ADHESION EQUIVALENT TO $SSTN_{VLA4}$. HMEC-1 endothelial cells were allowed to attach to the IIICS fragment of fibronectin (the VLA-4 binding site) for 2.5 hr at 37° C. in the presence of 0-30 µM $SSTN_{VLA4}$ or $SSTN_{I/V}$. The cells were fixed and the number of adherent cells was determined in triplicate wells, and plotted as a percentage of cells incubated in the absence of peptide. An identical adhesion assay was performed with CAG myeloma cells with similar results (not shown).

SSTN-I/V functions as effectively as $SSTN_{IGF1R}$ alone at myeloma cell killing (FIG. 14), and works as well as $SSTN_{VLA4}$ at blocking the adhesion of myeloma cells (not shown) or endothelial cells via VLA-4 (FIG. 15).

Figure 16:
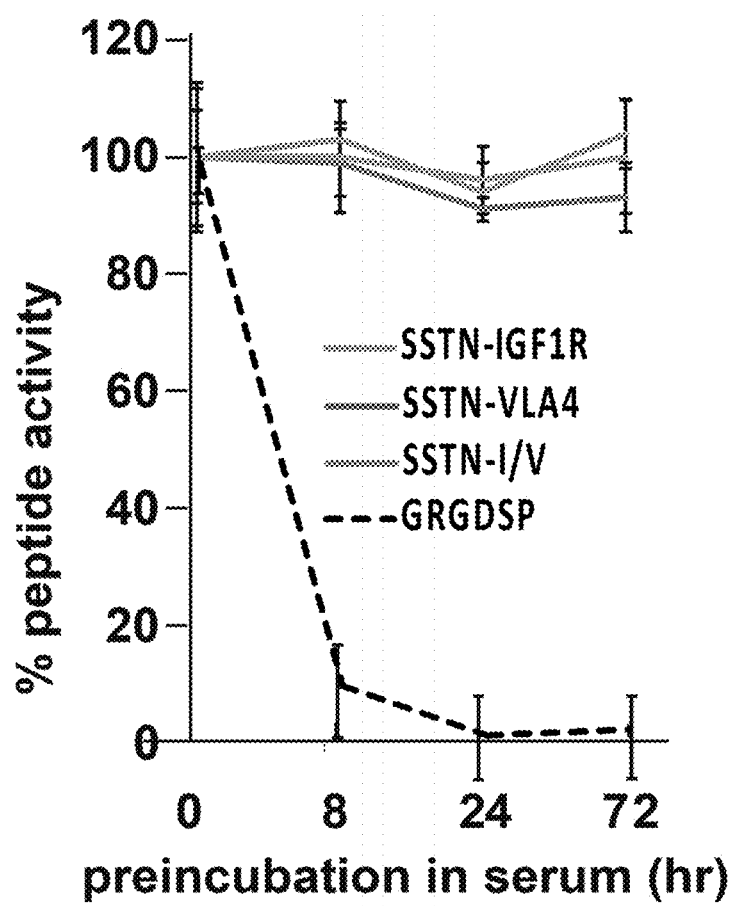
FIG. 16. $SSTN_{I/V}$ IS STABLE IN RODENT SERUM, EQUIVALENT TO $SSTN_{IGF1R}$ AND $SSTN_{VLA4}$. $SSTN_{I/V}$, $SSTN_{IGF1R}$ and $SSTN_{VLA4}$ were incubated at 37° C. for up to 72 hr in mouse serum. Note that rodent serum is known to contain substantial proteolytic activity against peptides. A GRGDSP integrin-inhibitory peptide was used as control, tested against endothelial cell adhesion to fibronectin. Either myeloma cell viability, or endothelial cell adhesion to IIICS fragment was used to test the activity of the SSTN peptides. SSTN peptides were used at up to 30 µM, and the GRGDSP peptide was used up to 1 mM. Activity observed in the assays was plotted against a standard curve to determine relative activity. Note that the GRGDSP peptide, like most peptides, is destroyed within a matter of a few hr, whereas the SSTN peptides retain full activity even after 3 days.

The inventors also examined whether $SSTN_{I/V}$ would retain the remarkable stability of $SSTN_{IGF1R}$ observed in serum. Serum or plasma contains proteases that rapidly destroy peptides, and for this reason investigators often need to continually replenish peptides in culture medium (contains 10% serum) when treating cells. It is also why peptides are rapidly destroyed once in the patient's plasma in vivo. However, the inventors find $SSTN_{IGF1R}$ is 100% stable in human plasma, bovine serum or mouse serum for more than 3 days at 37° C. (FIG. 16). Testing of $SSTN_{I/V}$ and $SSTN_{VLA4}$ reveals that both peptides are also 100% stable in mouse serum for 3 days at 37° C. In comparison, an RGDSP peptide that inhibits integrin-mediated adhesion was used as a control and found to be completely inactivated within 8 hr.

Figure 17:
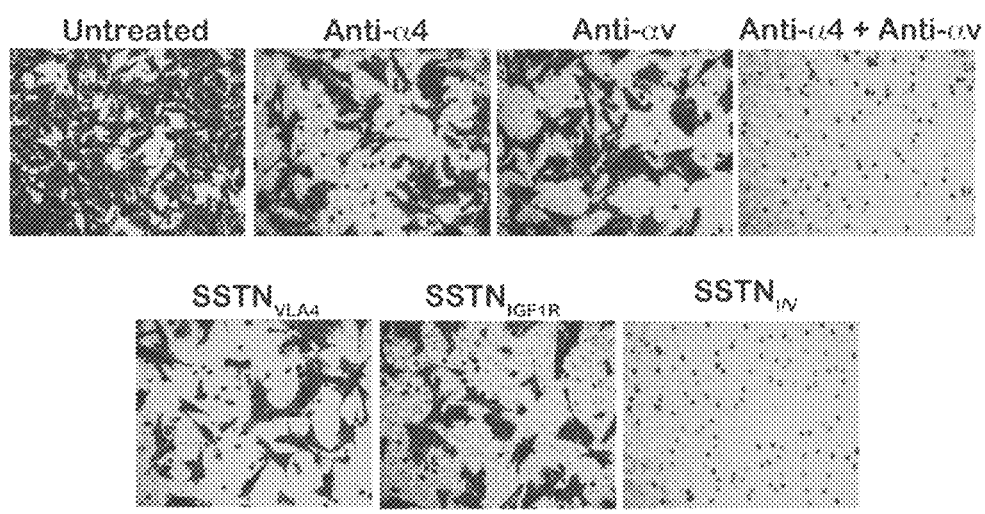
FIG. 17. $SSTN_{I/V}$ BLOCKS INVASION OF MOUSE MELANOMA CELLS ON THE VLA-4 LIGAND FIBRONECTIN. M21 murine melanoma cells are allowed to migrate for 16 hr through filters coated with fibronectin. The relative roles of the αvβ3 integrin and the α4β1 integrin (VLA-4) are determined using blocking antibodies to αv and α4 integrin subunits, or both antibodies combined. Also shown is inhibition with 30 µM $SSTN_{IGF1R}$, which mimics the partial block observed with αvβ3-blocking antibody, with 30 µM $SSTN_{VLA4}$, which duplicates partial block observed with the α4β1 blocking antibody, and 30 µM $SSTN_{I/V}$, which contains the activities of both peptides and blocks both integrins, completely preventing cell invasion.
Figure 18:
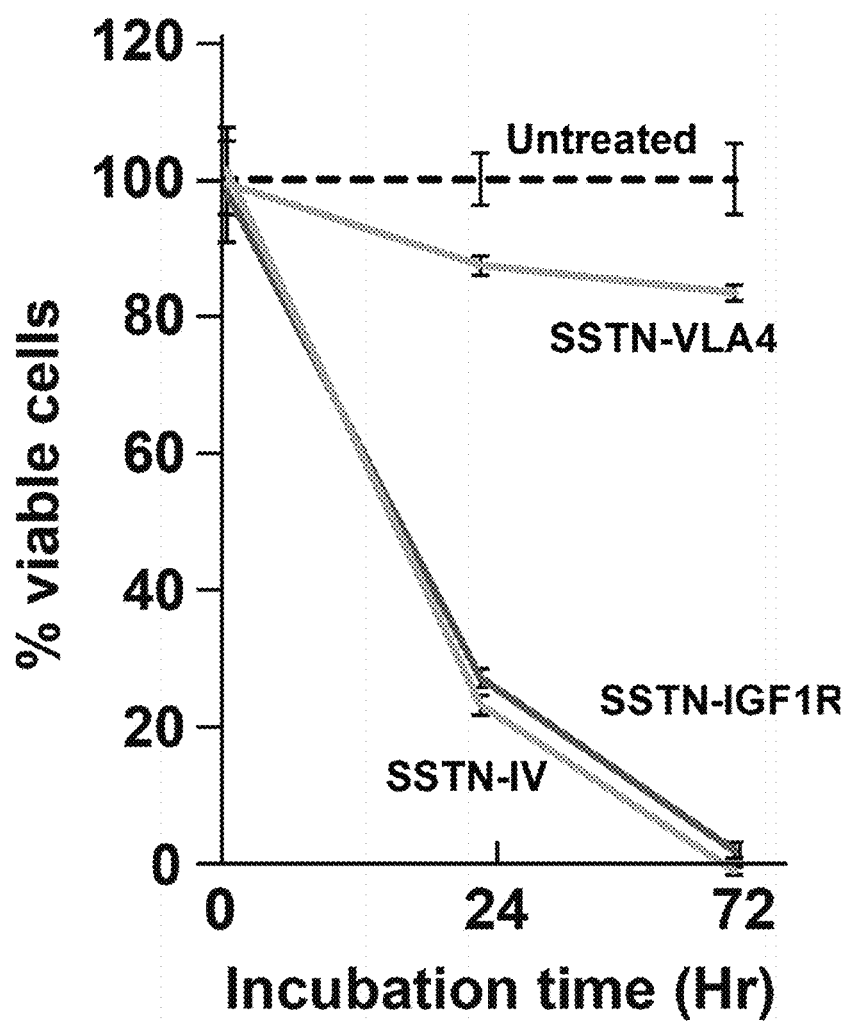
FIG. 18. $SSTN_{I/V}$ BLOCKS SURVIVAL OF MOUSE MELANOMA CELLS. B78 murine melanoma cells grown in serum-containing DMEM are incubated for up to 72 hr in 30 µM $SSTN_{VLA4}$, $SSTN_{IGF1R}$ or $SSTN_{I/V}$, then viable cells were quantified by trypan blue exclusion. Note that whereas $SSTN_{VLA4}$ has only a minimal effect on cell survival, the cells are killed by $SSTN_{IGF1R}$ and $SSTN_{I/V}$ mimics this activity.

Melanoma is an insidious form of skin cancer and melanoma cells express Sdc1, IGF-1R, the αvβ3 integrin, VLA-4 and VEGFR2, all the receptors involved in the signaling complexes targeted by $SSTN_{I/V}$. The inventors have therefore tested whether melanoma cells rely on these receptors and their organization by Sdc1, by testing the efficacy of the $SSTN_{I/V}$ peptide on melanoma invasion through filters coated with fibronectin, a ligand for the avb3 and VLA-4, and on melanoma cell survival. The inventors find that $SSTN_{IGF1R}$ and $SSTN_{VLA4}$ each partially block the invasion of melanoma cells by blocking their respective integrin, whereas $SSTN_{I/V}$ achieves a total block (FIG. 17). In a survival assay, the inventors also find that $SSTN_{I/V}$ blocks the mouse melanoma cell survival over a period of 72 hr (FIG. 18), utilizing the IGF-1R blocking activity inherent in the peptide, as survival is also blocked by $SSTN_{IGF1R}$, but only minimally by $SSTN_{VLA4}$.

Example 3—Use of the Peptide in Treatment

In this prophetic example, we provide further guidance for treating a subject in need with the disclosed fusion peptides.

SSTN-I/V in sterile saline is expected to have a half-life of sufficient duration (ca. 24 hr) that it can be used to treat subjects via twice weekly or weekly injection. In the case of the subject being an experimental mouse bearing a tumor xenograft susceptible to SSTN-I/V, it is anticipated that injection of the drug at dose equivalent to 1.5-15 mg/kg/day (e.g., injection of 14 mg to achieve the low dose if performed weekly) will be sufficient to reduce growth of the tumor. In the case of a human, in which the dose can often be extrapolated from the mouse dose using the body mass formula of Reagan-Shaw et al. (FASEB J. 22: 659 (2007)), treatment dose is predicted to be 0.12-1.2 mg/kg/day.

As the skilled artisan would recognize, treatment of a human usually involves starting at a low dose and discovering the effective dose from there, with the effective dosage often correlated with body mass. All suggested human dosage ranges disclosed herein are non-limiting examples. Based on the guidance given in this application, the skilled artisan could determine the effective dosage through the type of experimentation that is routinely done in the art.

All of the compositions and/or methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and/or methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

REFERENCES

The following references, to the extent that they provide exemplary procedural or other details supplementary to those set forth herein, are specifically incorporated herein by reference.

Ades, E. W., et al., *J. Invest. Dermatol.*, 99:683-690, 1992.
Alexander et al., *Nat. Genet.*, 25:329-332, 2000.
Anttonen et al., *Br. J. Cancer,* 79:558-564, 1999.
Ausubel et al., *In: Current Protocols in Molecular Biology*, John, Wiley & Sons, Inc, New York, 1994.
Baichwal and Sugden, *In: Gene Transfer*, Kucherlapati (Ed.), New York, Plenum Press, 117-148, 1986.
Barany and Merrifield, *In: The Peptides*, Gross and Meienhofer (Eds.), Academic Press, New York, pp. 1-284 1979.
Barbareschi et al., *Cancer,* 98:474-483, 2003.
Baserga et al., *Biochim Biophys Acta*, 1332: F105-126, 1997.
Beauvais and Rapraeger, *Exp. Cell Res.*, 286:219-232, 2004.
Beauvais and Rapraeger, *J. Cell Sci.*, 123:3796-3807, 2010.
Beauvais and Rapraeger, *Reprod. Biol. Endocrinol.*, 2:3, 2004.
Beauvais et al., *J. Cell Biol.*, 167(1):171-81, 2004.
Beauvais et al., *J. Exp. Med.*, 206:691-705, 2009.
Beauvais et al., *Cancer Res.*, 76(17):4982-4993, 2016.
Bernfield et al., *Annu. Rev. Biochem.*, 68:729-777, 1999.
Brooks et al., *Cell,* 79:1157-1164, 1994.
Brooks et al., *J. Clin. Invest.*, 99:1390-1398, 1997.
Brooks et al., *Science*, 264:569-571, 1994.
Burbach et al., *Matrix Biol.*, 22:163-177, 2003.
Cantor et al., *Cancer Immunol. Res.*, 3:661-667, 2015.
Carman and Springer, *Curr. Opin. Cell Biol.*, 15:547-556, 2003.
Chitnis et al., *Clin. Cancer Res.*, 14:6364-6370, 2008.
Choi et al., *J. Biol. Chem.*, 280:42573-42579, 2005.
Choi et al., *J. Biol. Chem.*, 290:16943-16953, 2015.
Conejo et al., *Int. J. Cancer,* 88:12-20, 2000.
Coupar et al., *Gene*, 68:1-10, 1988.
Dallas et al., *Cancer Metastasis Rev.*, 26:433-441, 2007.
De et al., *J. Biol. Chem.*, 278:39044-39050, 2003.
Dhanasekaran and Reddy, *Oncogene*, 27:6245-6251, 2008.
Elfenbein and Simons, *J. Cell Sci.*, 126:3799-3804, 2013.
Ellis and Hicklin, *Nat. Rev. Cancer,* 8:579-591, 2008.
Eliceiri and Cheresh, *J. Clin. Invest.*, 103:1227-1230, 1999.
Eliceiri et al., *J. Cell Biol.*, 140:1255-1263, 1998.
Eliceiri, *Circ. Res.*, 89:1104-1110, 2001.
Fechheimer et al., *Proc. Natl. Acad. Sci. USA*, 84:8463-8467, 1987.
Felding-Habermann and Cheresh, *Curr. Opin. Cell. Biol.*, 5:864-868, 1993.
Felding-Habermann et al., *Proc. Natl. Acad. Sci. USA*, 98:1853-1858, 2001.
Fontanella et al., *Ann. Transl. Med.*, 2:123, 2014.
Fraley et al., *Proc. Natl. Acad. Sci. USA*, 76:3348-3352, 1979.
Friedlander et al., *Science,* 270:1500-1502, 1995.
Friedmann, *Science*, 244:1275-1281, 1989.
Fujiya et al., *Jpn. J Cancer Res.*, 92:1074-1081, 2001.
Galvan et al., *J. Biol. Chem.*, 278:13325-13332, 2003.
Garmy-Susini et al., *Cancer Res.*, 70:3042-3051, 2010.
Garmy-Susini et al., *J. Clin. Invest.*, 115:1542-1551, 2005.
Giancotti and Ruoslahti, *Science*, 285:1028-1032, 1999.
Gingis-Velitski et al., *J. Biol. Chem.*, 279:23536-23541, 2004.
Goldfinger et al., *Circ. Res.*, 103:177-185, 2008.
Graham and Van Der Eb, *Virology*, 52:456-467, 1973.
Han et al., *J. Biol. Chem.*, 276:40903-40909, 2001.
Han et al., *J. Biol. Chem.*, 278:34845-34853, 2003.
Hayakawa et al., *Microbes Infect.*, 8:1098-1107, 2006.
Harland and Weintraub, *J. Cell Biol.*, 101:1094-1099, 1985.
Hermonat and Muzycska, *Proc. Natl. Acad. Sci. USA*, 81:6466-6470, 1984.
Hood et al., *J. Cell Biol.*, 162:933-943, 2003.
Inki et al., *Br. J. Cancer,* 70:319-323, 1994.
Johnson et al., *In: Biotech. Pharm.*, Pezzuto et al. (Eds.), Chapman and Hall, N Y, 1993.
Jones et al., *J. Oral. Pathol. Med.*, 26:63-68, 1997.
Jung et al., *Oncogenesis*, 5:e202, 2016.
Kaeppler et al., *Plant Cell Reports* 9: 415-418, 1990.
Kaneda et al., *Science*, 243:375-378, 1989.
Kerbel, *N. Engl. J. Med.*, 358:2039-2049, 2008.
Kim et al., *Mol. Biol. Cell,* 5:797-805, 1994.
Klass et al., *J. Cell Sci.*, 113:493-506, 2000.
Klatka, *Eur. Arch. Otorhinolaryngol.*, 259:115-118, 2002.
Kumar et al., *Leukemia*, 17:2025-2031, 2003.
Kumar-Singh et al., *J. Pathol.*, 186:300-305, 1998.
Kwon et al., *J. Biol. Chem.*, 290:5772-5782, 2015.
Kyte and Doolittle, *J Mol Biol*, 157(1):105-32, 1982.
Lacal et al., *Int. J. Oncol.*, 27:1625-1632, 2005.
Lebakken et al., *Exp. Cell Res.*, 259:315-325, 2000.
Lebakken and Rapraeger, *J. Cell Biol.*, 132:1209-1221, 1996.
Leppanen et al., *Proc. Natl. Acad. Sci. U.S.A,* 107:2425-2430, 2010.
Levy et al., *Br. J. Cancer,* 74:423-431, 1996.
Levy et al., *Bull. Cancer,* 84:235-237, 1997.
Liapis et al., *Diagn. Mol. Pathol.*, 5:127-135, 1996.
Lin et al., *Blood,* 120:1039-1047, 2012.
Lu et al., *J. Natl. Cancer Inst.*, 93:1852-1857, 2001.
Mahabeleshwar et al., *J. Exp. Med.*, 203:2495-2507, 2006.
Mahabeleshwar et al., *Circ. Res.*, 101:570-580, 2007.
Maniatis, et al., In: *Molecular Cloning*, A Laboratory Manual, Cold Spring Harbor Press, N Y, 1990.
Matsumoto et al., *Int. J. Cancer,* 74:482-491, 1997.
McFall and Rapraeger, *J. Biol. Chem.*, 272:12901-12904, 1997.
McFall and Rapraeger, *J. Biol. Chem.*, 273:28270-28276, 1998.
Merrifield, *Science,* 232: 341-347, 1986.
Miranti and Brugge, *Nat. Cell Biol.*, 4:E83-90, 2002.
Nakaerts et al., *Int. J. Cancer,* 74:335-345, 1997.
Nakanishi et al., *Intl. J. Cancer,* 80:527-532, 1999.
Nishiya et al., *Nat. Cell. Biol.*, 7:343-352, 2005.
Mestas and Ley, *Trends Cardiovasc. Med.*, 18:228-232, 2008.
Millard et al., *Theranostics*, 1:154-188, 2011.
Nagy et al., *Annu. Rev. Pathol.*, 2:251-275, 2007.
Nicolau and Sene, *Biochim. Biophys. Acta,* 721:185-190, 1982.
Nicolau et al., *Methods Enzymol.*, 149:157-176, 1987.
Oh et al., *J. Biol. Chem.*, 272:11805-11811, 1997b.
Oh et al., *J. Biol. Chem.*, 272:8133-8136, 1997a.
Oh et al., *J. Biol. Chem.*, 273:10624-10629, 1998.
Pasqualini et al., *J. Cell Sci.*, 105(Pt 1):101-11, 1993.
PCT Appln. WO 94/09699
PCT Appln. WO 95/06128
Petitclerc et al., *Cancer Res.*, 59:2724-2730, 1999.
Pilch et al., *J. Biol. Chem.*, 277:21930-21938, 2002.
Plow et al., *J. Biol. Chem.*, 275:21785-21788, 2000.
Potrykus et al., *Mol. Gen. Genet.*, 199:183-188, 1985.

Potter et al., *Proc. Natl. Acad. Sci. USA*, 81:7161-7165, 1984.
Pulkkinen et al., *Acta Otolaryngol.*, 117:312-315, 1997.
Rapraeger, *J. Cell. Biol.*, 149:995-998, 2000.
Rapraeger, *FEBS J.*, 280:2207-2215, 2013.
Rapraeger et al., *FEBS J.*, 280:2194-2206, 2013.
Rapraeger et al., *J. Cell Biol.*, 103:2683-2696, 1986.
Ratnikov et al., *J. Biol. Chem.*, 277:7377-7385, 2002.
Remington's Pharmaceutical Sciences, 15$^{th}$ ed., pages 1035-1038 and 1570-1580, Mack Publishing Company, Easton, Pa., 1980.
Ridgeway, In: *Vectors: A survey of molecular cloning vectors and their uses*. Rodriguez and Denhardt (Eds.), Stoneham, Butterworth, 467-492, 1988.
Rintala et al., *Gynecol. Onol.*, 75:372-378, 1999.
Roskelley et al., *Curr. Opin. Cell Biol.*, 7:736-747, 1995.
Sambrook et al., In: *Molecular Cloning, A Laboratory Manual*, 3rd Ed., Cold Spring Harbor Press, NY, 2001.
Sanderson and Bernfield, *Proc. Natl. Acad. Sci. USA*, 85:9562-9566, 1988.
Schlingemann and van Hinsbergh, *Br. J. Ophthalmol.*, 81:501-512, 1997.
Soukka et al., *J Oral Pathol. Med.*, 29:308-313, 2000.
Stanley et al., *Am. J. Clin. Pathol.*, 112:377-383, 1999.
Stewart and Young, In: *Solid Phase Peptide Synthesis*, 2d. Ed., Pierce Chemical Co. 1984.
Tam et al., *J. Am. Chem. Soc.*, 105:6442, 1983.
Tonn et al., *Anticancer Res.*, 18:2599-2605, 1998.
Tur-Kaspa et al., *Mol. Cell Biol.*, 6:716-718, 1986.
U.S. Pat. No. 4,196,265
U.S. Pat. No. 4,554,101
U.S. Pat. No. 4,683,202
U.S. Pat. No. 5,302,523
U.S. Pat. No. 5,322,783
U.S. Pat. No. 5,384,253
U.S. Pat. No. 5,399,363
U.S. Pat. No. 5,440,013
U.S. Pat. No. 5,446,128
U.S. Pat. No. 5,464,765
U.S. Pat. No. 5,466,468
U.S. Pat. No. 5,475,085
U.S. Pat. No. 5,538,877
U.S. Pat. No. 5,538,880
U.S. Pat. No. 5,543,158
U.S. Pat. No. 5,550,318
U.S. Pat. No. 5,563,055
U.S. Pat. No. 5,580,859
U.S. Pat. No. 5,589,466
U.S. Pat. No. 5,610,042
U.S. Pat. No. 5,618,914
U.S. Pat. No. 5,641,515
U.S. Pat. No. 5,656,610
U.S. Pat. No. 5,670,155
U.S. Pat. No. 5,672,681
U.S. Pat. No. 5,674,976
U.S. Pat. No. 5,702,932
U.S. Pat. No. 5,710,245
U.S. Pat. No. 5,736,524
U.S. Pat. No. 5,780,448
U.S. Pat. No. 5,789,215
U.S. Pat. No. 5,840,833
U.S. Pat. No. 5,846,225
U.S. Pat. No. 5,846,233
U.S. Pat. No. 5,859,184
U.S. Pat. No. 5,928,906
U.S. Pat. No. 5,929,237
U.S. Pat. No. 5,945,100
U.S. Pat. No. 5,981,274
U.S. Pat. No. 5,994,624
van der Flier and Sonnenberg, *Cell Tissue Res.*, 305:285-298, 2001.
Wiksten et al., *Int. J. Cancer*, 95:1-6, 2001.
Wang et al., *J. Biol. Chem.*, 289:30318-30332, 2014.
Wang et al., *J. Biol. Chem.*, 290:26103-26113, 2015.
Wang et al., *J. Biol. Chem.*, 285:13569-13579, 2010.
Wong et al., *Gene*, 10:87-94, 1980.
Woods and Couchman, *Curr. Opin. Cell Biol.*, 13:578-583, 2001.
Wu and Wu, *J. Biol. Chem.*, 262:4429-4432, 1987.
Wu and Wu, *Biochemistry*, 27:887-892, 1988.
Yang et al., *Cancer Res.*, 71:5512-5521, 2011.
Yang et al., *Proc. Natl. Acad. Sci. U.S.A.*, 107:1906-1911, 2010.
Yusuf-Makagiansar et al., *Med. Res. Rev.*, 22:146-167, 2002.
Zetter, B. R., *Annu. Rev. Med.*, 49:407-424, 1998.
Zimmermann et al., *Dev. Cell*, 9:377-388, 2005.

---

We claim:

1. A fusion peptide of from 39 to 100 amino acid residues in length that comprises:
   (a) an IGF-1R-binding segment consisting of SEQ ID NO:1; and
   (b) a VLA-4-binding segment consisting of SEQ ID NO:2.

2. The fusion peptide of claim 1, wherein the fusion peptide is 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 or 100 amino acid residues in length.

3. The fusion peptide of claim 1, wherein the fusion peptide consists essentially of the IGF-1R-binding segment and the VLA-4-binding segment.

4. The fusion peptide of claim 1, wherein the fusion peptide comprises a segment consisting of SEQ ID NO:3.

5. The fusion peptide of claim 1, wherein the fusion peptide comprises a linker interposed between the IGF-1R-binding segment and the VLA-4-binding segment.

6. The fusion peptide of claim 5, wherein the linker comprises a glutamate residue (E) attached directly to the C-terminus (Q residue) of the IGF-1R-binding segment.

7. The fusion peptide of claim 5, wherein the linker comprises one or more alanine (A) residues.

8. A nucleic acid segment encoding the fusion peptide of claim 1.

9. A pharmaceutical composition comprising (a) the fusion peptide of claim 1, and (b) a pharmaceutically acceptable buffer, diluent or excipient.

10. A method of inhibiting interaction of syndecan 1 with VLA-4 and/or IGF-1R comprising contacting a cell expressing VLA-4 and/or IGF-1R with the fusion peptide of claim 1, whereby the interaction of syndecan 1 with VLA-4 and/or IGF-1R is inhibited.

11. The method of claim 10, wherein the cell is a cancer cell, and wherein the method facilitates the death of the cancer cell.

12. The method of claim 11, wherein the cancer cell is a carcinoma, a myeloma, a melanoma or a glioma.

13. The method of claim 10, wherein the cell is an immune cell.

14. The method of claim 13, wherein the immune cell is a leukocyte.

15. A method of treating a subject with a cancer, cells of which express VLA-4 and/or IGF-1R, comprising contacting one or more of the cells with the fusion peptide of claim 1, whereby the cancer is effectively treated.

16. The method of claim 15, wherein the subject is a human.

17. The method of claim 15, wherein the cancer cell is a carcinoma, a myeloma, a melanoma or a glioma.

18. A method of inhibiting an autoimmune disease in a subject comprising administering to the subject the fusion peptide of claim 1.

19. The method of claim 18, wherein the subject is a human.

20. The method of claim 18, wherein the autoimmune disease is rheumatoid arthritis, systemic lupus erythematous, Sjogrens's disease, Crohn's disease, ulcerative colitis, psoratic arthritis, multiple sclerosis or ankylosing spondylitis.

* * * * *

SEQUENCE LISTING

<160> NUMBER OF SEQ ID NOS: 38

<210> SEQ ID NO 1
<211> LENGTH: 27
<212> TYPE: PRT
<213> ORGANISM: Homo sapiens

<400> SEQUENCE: 1

Leu Pro Ala Gly Glu Gly Pro Lys Glu Gly Glu Ala Val Val Leu Pro
1               5                   10                  15

Glu Val Glu Pro Gly Leu Thr Ala Arg Glu Gln
            20                  25

<210> SEQ ID NO 2
<211> LENGTH: 12
<212> TYPE: PRT
<213> ORGANISM: Homo sapiens

<400> SEQUENCE: 2

```
Asp Phe Thr Phe Glu Thr Ser Gly Glu Asn Thr Ala
1               5                   10
```

<210> SEQ ID NO 3
<211> LENGTH: 39
<212> TYPE: PRT
<213> ORGANISM: Artificial Sequence
<220> FEATURE:
<223> OTHER INFORMATION: Fusion protein that includes two peptides from
      homo sapiens.

<400> SEQUENCE: 3

```
Leu Pro Ala Gly Glu Gly Pro Lys Glu Gly Glu Ala Val Val Leu Pro
1               5                   10                  15

Glu Val Glu Pro Gly Leu Thr Ala Arg Glu Gln Asp Phe Thr Phe Glu
            20                  25                  30

Thr Ser Gly Glu Asn Thr Ala
        35
```

<210> SEQ ID NO 4
<211> LENGTH: 4
<212> TYPE: PRT
<213> ORGANISM: Artificial Sequence
<220> FEATURE:
<223> OTHER INFORMATION: Linker sequence.

<400> SEQUENCE: 4

```
Ala Ala Ala Ala
1
```

<210> SEQ ID NO 5
<211> LENGTH: 5
<212> TYPE: PRT
<213> ORGANISM: Artificial Sequence
<220> FEATURE:
<223> OTHER INFORMATION: Linker sequence.

<400> SEQUENCE: 5

```
Glu Ala Ala Ala Ala
1               5
```

<210> SEQ ID NO 6
<211> LENGTH: 28
<212> TYPE: PRT
<213> ORGANISM: Homo sapiens

<400> SEQUENCE: 6

```
Leu Pro Ala Gly Glu Gly Pro Lys Glu Gly Glu Ala Val Val Leu Pro
1               5                   10                  15

Glu Val Glu Pro Gly Leu Thr Ala Arg Glu Gln Glu
            20                  25
```

<210> SEQ ID NO 7
<211> LENGTH: 32
<212> TYPE: PRT
<213> ORGANISM: Homo sapiens

<400> SEQUENCE: 7

```
Ser Thr Ser Thr Leu Pro Ala Gly Glu Gly Pro Lys Glu Gly Glu Ala
1               5                   10                  15

Val Val Leu Pro Glu Val Glu Pro Gly Leu Thr Ala Arg Glu Gln Glu
            20                  25                  30
```

<210> SEQ ID NO 8

```
<211> LENGTH: 26
<212> TYPE: PRT
<213> ORGANISM: Homo sapiens

<400> SEQUENCE: 8

Leu Pro Ala Gly Glu Gly Pro Lys Glu Gly Ala Val Val Leu Pro
1               5                   10                  15
Glu Val Glu Pro Gly Leu Thr Ala Arg Glu
            20                  25

<210> SEQ ID NO 9
<211> LENGTH: 25
<212> TYPE: PRT
<213> ORGANISM: Homo sapiens

<400> SEQUENCE: 9

Leu Pro Ala Gly Glu Gly Pro Lys Glu Gly Ala Val Val Leu Pro
1               5                   10                  15
Glu Val Glu Pro Gly Leu Thr Ala Arg
            20                  25

<210> SEQ ID NO 10
<211> LENGTH: 27
<212> TYPE: PRT
<213> ORGANISM: Homo sapiens

<400> SEQUENCE: 10

Pro Ala Gly Glu Gly Pro Lys Glu Gly Glu Ala Val Val Leu Pro Glu
1               5                   10                  15
Val Glu Pro Gly Leu Thr Ala Arg Glu Gln Glu
            20                  25

<210> SEQ ID NO 11
<211> LENGTH: 26
<212> TYPE: PRT
<213> ORGANISM: Homo sapiens

<400> SEQUENCE: 11

Ala Gly Glu Gly Pro Lys Glu Gly Glu Ala Val Val Leu Pro Glu Val
1               5                   10                  15
Glu Pro Gly Leu Thr Ala Arg Glu Gln Glu
            20                  25

<210> SEQ ID NO 12
<211> LENGTH: 27
<212> TYPE: PRT
<213> ORGANISM: Homo sapiens

<400> SEQUENCE: 12

Asp Phe Thr Phe Glu Thr Ser Gly Glu Asn Thr Ala Val Val Ala Val
1               5                   10                  15
Glu Pro Asp Arg Arg Asn Gln Ser Pro Val Asp
            20                  25

<210> SEQ ID NO 13
<211> LENGTH: 4
<212> TYPE: PRT
<213> ORGANISM: Homo sapiens

<400> SEQUENCE: 13

Asp Phe Thr Phe
1
```

<210> SEQ ID NO 14
<211> LENGTH: 24
<212> TYPE: PRT
<213> ORGANISM: Homo sapiens

<400> SEQUENCE: 14

Asp Phe Thr Phe Glu Thr Ser Gly Glu Asn Thr Ala Val Val Ala Val
1               5                   10                  15

Glu Pro Asp Arg Arg Asn Gln Ser
            20

<210> SEQ ID NO 15
<211> LENGTH: 27
<212> TYPE: PRT
<213> ORGANISM: Homo sapiens

<400> SEQUENCE: 15

Glu Thr Ser Gly Glu Asn Thr Ala Val Val Ala Val Glu Pro Asp Arg
1               5                   10                  15

Arg Asn Gln Ser Pro Val Asp Gln Gly Ala Thr
            20                  25

<210> SEQ ID NO 16
<211> LENGTH: 31
<212> TYPE: PRT
<213> ORGANISM: Homo sapiens

<400> SEQUENCE: 16

Asp Phe Thr Phe Glu Thr Ser Gly Glu Asn Thr Ala Val Val Ala Val
1               5                   10                  15

Glu Pro Asp Arg Arg Asn Gln Ser Pro Val Asp Gln Gly Ala Thr
            20                  25                  30

<210> SEQ ID NO 17
<211> LENGTH: 20
<212> TYPE: PRT
<213> ORGANISM: Homo sapiens

<400> SEQUENCE: 17

Glu Thr Ser Gly Glu Asn Thr Ala Val Val Ala Val Glu Pro Asp Arg
1               5                   10                  15

Arg Asn Gln Ser
            20

<210> SEQ ID NO 18
<211> LENGTH: 8
<212> TYPE: PRT
<213> ORGANISM: Homo sapiens

<400> SEQUENCE: 18

Gly Leu Thr Ala Arg Glu Gln Glu
1               5

<210> SEQ ID NO 19
<211> LENGTH: 8
<212> TYPE: PRT
<213> ORGANISM: Homo sapiens

<400> SEQUENCE: 19

Ser Gly Glu Gln Asp Phe Thr Phe
1               5

<210> SEQ ID NO 20
<211> LENGTH: 8
<212> TYPE: PRT
<213> ORGANISM: Mus musculus

<400> SEQUENCE: 20

Gly Phe Thr Ala Arg Asp Lys Glu
1               5

<210> SEQ ID NO 21
<211> LENGTH: 8
<212> TYPE: PRT
<213> ORGANISM: Rattus norvegicus

<400> SEQUENCE: 21

Asp Phe Thr Ala Arg Asp Lys Glu
1               5

<210> SEQ ID NO 22
<211> LENGTH: 8
<212> TYPE: PRT
<213> ORGANISM: Macaca mulatta

<400> SEQUENCE: 22

Asp Leu Thr Ala Arg Glu Gln Glu
1               5

<210> SEQ ID NO 23
<211> LENGTH: 8
<212> TYPE: PRT
<213> ORGANISM: Hylobates lar

<400> SEQUENCE: 23

Gly Leu Thr Ala Arg Glu Glu Glu
1               5

<210> SEQ ID NO 24
<211> LENGTH: 8
<212> TYPE: PRT
<213> ORGANISM: Mesocricetus auratus

<400> SEQUENCE: 24

Ser Ser Thr Thr Trp Asp Lys Glu
1               5

<210> SEQ ID NO 25
<211> LENGTH: 8
<212> TYPE: PRT
<213> ORGANISM: Orcinus orca

<400> SEQUENCE: 25

Gly Leu Thr Ala Gln Glu Lys Glu
1               5

<210> SEQ ID NO 26
<211> LENGTH: 14
<212> TYPE: PRT
<213> ORGANISM: Homo sapiens

<400> SEQUENCE: 26

Glu Gln Asp Phe Thr Phe Glu Thr Ser Gly Glu Asn Thr Ala
1               5                   10

<210> SEQ ID NO 27
<211> LENGTH: 57

```
<212> TYPE: PRT
<213> ORGANISM: Artificial Sequence
<220> FEATURE:
<223> OTHER INFORMATION: Fusion protein containing two different homo
      sapiens peptide fragments.

<400> SEQUENCE: 27

Leu Pro Ala Gly Glu Gly Pro Lys Glu Gly Glu Ala Val Val Leu Pro
1               5                   10                  15

Glu Val Glu Pro Gly Leu Thr Ala Arg Glu Gln Glu Ala Ala Ala Ala
            20                  25                  30

Asp Phe Thr Phe Glu Thr Ser Gly Glu Asn Thr Ala Val Val Ala Val
        35                  40                  45

Glu Pro Asp Arg Arg Asn Gln Ser
    50                  55

<210> SEQ ID NO 28
<211> LENGTH: 44
<212> TYPE: PRT
<213> ORGANISM: Artificial Sequence
<220> FEATURE:
<223> OTHER INFORMATION: Fusion protein containing two different homo
      sapiens peptides.

<400> SEQUENCE: 28

Leu Pro Ala Gly Glu Gly Pro Lys Glu Gly Glu Ala Val Val Leu Pro
1               5                   10                  15

Glu Val Glu Pro Gly Leu Thr Ala Arg Glu Gln Glu Ala Ala Ala Ala
            20                  25                  30

Asp Phe Thr Phe Glu Thr Ser Gly Glu Asn Thr Ala
        35                  40

<210> SEQ ID NO 29
<211> LENGTH: 36
<212> TYPE: PRT
<213> ORGANISM: Artificial Sequence
<220> FEATURE:
<223> OTHER INFORMATION: Fusion protein containing two different homo
      sapiens peptides.

<400> SEQUENCE: 29

Leu Pro Ala Gly Glu Gly Pro Lys Glu Gly Glu Ala Val Val Leu Pro
1               5                   10                  15

Glu Val Glu Pro Gly Leu Thr Ala Arg Glu Gln Glu Ala Ala Ala Ala
            20                  25                  30

Asp Phe Thr Phe
        35

<210> SEQ ID NO 30
<211> LENGTH: 52
<212> TYPE: PRT
<213> ORGANISM: Artificial Sequence
<220> FEATURE:
<223> OTHER INFORMATION: Fusion protein containing two different homo
      sapiens peptides.

<400> SEQUENCE: 30

Leu Pro Ala Gly Glu Gly Pro Lys Glu Gly Glu Ala Val Val Leu Pro
1               5                   10                  15

Glu Val Glu Pro Gly Leu Thr Ala Arg Glu Gln Asp Phe Thr Phe Glu
            20                  25                  30

Thr Ser Gly Glu Asn Thr Ala Val Val Ala Val Glu Pro Asp Arg Arg
        35                  40                  45
```

Arg Asn Gln Ser
    50

<210> SEQ ID NO 31
<211> LENGTH: 6
<212> TYPE: PRT
<213> ORGANISM: Artificial Sequence
<220> FEATURE:
<223> OTHER INFORMATION: Synthetic control peptide.

<400> SEQUENCE: 31

Gly Arg Gly Asp Ser Pro
1               5

<210> SEQ ID NO 32
<211> LENGTH: 6
<212> TYPE: PRT
<213> ORGANISM: Homo sapiens

<400> SEQUENCE: 32

Leu Ile Val Leu Phe Leu
1               5

<210> SEQ ID NO 33
<211> LENGTH: 7
<212> TYPE: PRT
<213> ORGANISM: Homo sapiens

<400> SEQUENCE: 33

Val Ala Val Val Phe Leu Leu
1               5

<210> SEQ ID NO 34
<211> LENGTH: 6
<212> TYPE: PRT
<213> ORGANISM: Homo sapiens

<400> SEQUENCE: 34

Ala Gly Gly Ala Ile Val
1               5

<210> SEQ ID NO 35
<211> LENGTH: 10
<212> TYPE: PRT
<213> ORGANISM: Homo sapiens

<400> SEQUENCE: 35

Arg Met Lys Lys Lys Asp Glu Gly Ser Tyr
1               5                   10

<210> SEQ ID NO 36
<211> LENGTH: 10
<212> TYPE: PRT
<213> ORGANISM: Homo sapiens

<400> SEQUENCE: 36

Arg Met Arg Lys Lys Asp Glu Gly Ser Tyr
1               5                   10

<210> SEQ ID NO 37
<211> LENGTH: 4
<212> TYPE: PRT
<213> ORGANISM: Homo sapiens

<400> SEQUENCE: 37

```
Glu Phe Tyr Ala
1

<210> SEQ ID NO 38
<211> LENGTH: 20
<212> TYPE: PRT
<213> ORGANISM: Homo sapiens

<400> SEQUENCE: 38

Ser Leu Glu Glu Pro Lys Gln Ala Asn Gly Gly Ala Tyr Gln Lys Pro
1               5                   10                  15

Thr Lys Gln Glu
            20
```